(12) United States Patent
Besselievre et al.

(10) Patent No.: US 6,972,276 B1
(45) Date of Patent: *Dec. 6, 2005

(54) PROCESS FOR MAKING AMINE COMPOUNDS

(75) Inventors: Richard Besselievre, Burse sur Yvette (FR); Johan Smets, Lubbeek (BE); Jean Wevers, Steenhuffel (BE)

(73) Assignee: Procter & Gamble Company, Cincinnati, OH (US)

( * ) Notice: Subject to any disclaimer, the term of this patent is extended or adjusted under 35 U.S.C. 154(b) by 655 days.

This patent is subject to a terminal disclaimer.

(21) Appl. No.: 10/019,179

(22) PCT Filed: Jun. 23, 2000

(86) PCT No.: PCT/US00/17274

§ 371 (c)(1),
(2), (4) Date: Dec. 21, 2001

(87) PCT Pub. No.: WO01/04084

PCT Pub. Date: Jan. 18, 2001

(30) Foreign Application Priority Data

Jul. 9, 1999 (EP) .................................. 99401736
Apr. 12, 2000 (EP) .................................. 00870067

(51) Int. Cl.[7] ............................. C11D 3/50; A61K 7/46
(52) U.S. Cl. ............................ 510/101; 512/4; 512/27
(58) Field of Search ............................ 510/101; 512/2, 512/4, 27

(56) References Cited

U.S. PATENT DOCUMENTS

| | | |
|---|---|---|
| 3,426,011 A | 2/1969 | Parmeter et al. |
| 3,453,257 A | 7/1969 | Parmerter et al. |
| 3,453,258 A | 7/1969 | Parmerter et al. |
| 3,453,259 A | 7/1969 | Parmerter et al. |
| 3,453,260 A | 7/1969 | Parmerter et al. |
| 3,459,731 A | 8/1969 | Gramera et al. |
| 3,553,191 A | 1/1971 | Parmerter et al. |
| 3,565,887 A | 1/1971 | Parmerter et al. |
| 3,862,058 A | 1/1975 | Nirschl et al. |
| 3,936,448 A | 2/1976 | Lamberti |
| 3,948,790 A | 4/1976 | Speakman |
| 3,954,632 A | 5/1976 | Gloss |
| RE28,858 E * | 6/1976 | Litzinger ..................... 131/267 |
| 4,062,647 A | 12/1977 | Storm et al. |
| 4,174,291 A | 11/1979 | Benjamin et al. |
| 4,449,987 A | 5/1984 | Lindauer |
| 4,535,152 A | 8/1985 | Szejtli et al. |
| 4,565,647 A | 1/1986 | Llenado |
| 4,585,642 A | 4/1986 | Rieck |
| 4,616,008 A | 10/1986 | Hirai et al. |
| 4,638,058 A | 1/1987 | Brandt et al. |
| 4,664,839 A | 5/1987 | Rieck |
| 4,678,598 A | 7/1987 | Ogino et al. |
| 4,693,890 A | 9/1987 | Wilson et al. |
| 4,696,676 A | 9/1987 | Wilson et al. |
| 4,746,734 A | 5/1988 | Tsuchiyama et al. |
| 4,820,439 A | 4/1989 | Rieck |
| 4,853,369 A | 8/1989 | Mookherjee et al. |
| 4,933,371 A | 6/1990 | Hink et al. |
| 4,950,310 A | 8/1990 | Rieck |
| 5,009,239 A * | 4/1991 | Cohen et al. ................ 131/342 |
| 5,030,660 A | 7/1991 | Norris et al. |
| 5,188,753 A | 2/1993 | Schmidt et al. |
| 5,196,200 A | 3/1993 | Wilson et al. |
| 5,275,859 A * | 1/1994 | Phillips et al. .............. 428/66.6 |
| 5,378,414 A * | 1/1995 | Derkach ...................... 264/469 |

FOREIGN PATENT DOCUMENTS

| | | |
|---|---|---|
| EP | 011 340 | 11/1982 |
| EP | 313 146 B2 | 5/1993 |
| EP | 299 575 B1 | 1/1994 |
| EP | 659 876 | 6/1995 |
| EP | 090040687 | 2/1997 |
| EP | 971 021 A1 | 1/2000 |
| EP | 971 024 A1 | 1/2000 |
| EP | 971 026 A1 | 1/2000 |
| EP | 971 027 | 1/2000 |
| GB | 1261829 | 1/1972 |
| GB | 1379241 | 1/1975 |
| GB | 1387447 | 3/1975 |
| GB | 1389732 | 4/1975 |
| GB | 1398421 | 6/1975 |
| GB | 1398422 | 6/1975 |
| GB | 1425343 | 2/1976 |
| GB | 1439000 | 6/1976 |
| GB | 1514276 | 6/1978 |
| WO | WO 95/04809 A1 | 2/1995 |
| WO | WO 95/08976 A1 | 4/1995 |
| WO | WO 95/10591 A1 | 4/1995 |
| WO | WO 96/04940 A1 | 2/1996 |

(Continued)

OTHER PUBLICATIONS

Texier-Bouller, F, A Simple, Convenient and Mild Synthesis of Imines on Alumina Surface without solvent, Synthesis, 1985, p. 679-680.

(Continued)

*Primary Examiner*—John R. Hardee
(74) *Attorney, Agent, or Firm*—James F. McBride; Kim W. Zerby; Steve W. Miller

(57) ABSTRACT

There is provided a process for producing amine reaction product, in particular suitable for industrial process, whereby high yields of the amine reaction product is obtained. This is achieved by having a selected temperature range upon the contacting of the amine containing compound with the active aldehyde and/or ketone.

23 Claims, No Drawings

FOREIGN PATENT DOCUMENTS

| WO | WO 96/05358 A1 | 2/1996 |
| WO | WO 96/38528 | 12/1996 |
| WO | WO 98/40464 A1 | 9/1998 |

OTHER PUBLICATIONS

Psychophysics and Perfumery, pp. 243-250.
Steffen Arctander, Perfume and Flavor Chemicals, vol. I and II, 1969, Montclair, NJ USA.

B.D. Mookherjee et al., *Semio Activity of Flavor and Fragrance Molecules on Various Insect Species*, Bioactive Volatile Compounds from Plants, ASC Symposium Series 525, 1993, pp. 35-48.

Compilation of Odor and Taste Threshold Values Data, F.A. Fazzalari ed., 1978.

* cited by examiner

PROCESS FOR MAKING AMINE COMPOUNDS

FIELD OF THE INVENTION

The present invention relates to a process for producing amine reaction products.

BACKGROUND OF THE INVENTION

Perfumed products are well-known in the art. However, consumer acceptance of such perfumed products like laundry and cleaning products is determined not only by the performance achieved with these products but also by the aesthetics associated therewith. The perfume components are therefore an important aspect of the successful formulation of such commercial products.

It is also desired by consumers for treated fabrics to maintain the pleasing fragrance over time. Indeed, perfume additives make such compositions more aesthetically pleasing to the consumer, and in some cases the perfume imparts a pleasant fragrance to fabrics treated therewith. However, the amount of perfume carried-over from an aqueous laundry bath onto fabrics is often marginal and does not last long on the fabric. Furthermore, fragrance materials are often very costly and their inefficient use in laundry and cleaning compositions and ineffective delivery to fabrics results in a very high cost to both consumers and laundry and cleaning manufacturers. Industry, therefore, continues to seek with urgency for more efficient and effective fragrance delivery in laundry and cleaning products, especially for improvement in the provision of long-lasting fragrance to the fabrics.

One solution is to use carrier mechanisms for perfume delivery, such as by encapsulation. This is taught in the prior art and described in U.S. Pat. No. 5,188,753.

Still another solution is to formulate compounds which provide a delayed release of the perfume over a longer period of time than by the use of the perfume itself.

Disclosure of such compounds may be found in WO 95/04809, WO 95/08976 and co-pending application EP 95303762.9.

However, notwithstanding the advances in the art, there is still a need for a compound which provides a delayed release of the perfume component.

That need is even more acute for perfume ingredients which are characteristic of the fresh notes, namely the aldehydes and ketones perfume ingredients. Indeed, whilst these provide a fresh fragrance, these perfumes are also very volatile and have a low substantivity on the surface to be treated like fabrics.

It has recently been found that an amine reaction product of a compound containing a primary amine functional group and an active ketone or aldehyde containing component, such as imines compounds, fulfills such a need.

Disclosure of such compounds can be found in recently filed applications EP 98870227.0, EP 98870226.2, EP 99870026.4, and EP 99870025.6, all incorporated herein by reference.

Imine compounds are known in the art under the name of Schiff bases which is the condensation of an aldehyde perfume ingredient with an anthranilate. A typical description can be found in U.S. Pat. No. 4,853,369. By means of this compound, the aldehyde perfume is made substantive to the fabrics. However, a problem encountered with these Schiff bases is that the methylanthranilate compound also exhibits a strong scent, which as a result produces a mixture of fragrances, thereby reducing or even inhibiting the aldehyde fragrance perception. Further, Schiff-bases produced by such patents requires the use of a high reaction temperature of from 90 to 150° C. Not to be bound by theory, it is believed that the high temperature which is used for the reaction is less favoured as it tends to oxidize the volatile perfume ingredient of consideration.

Still another solution is the use of a glucosamine as described in JP 09040687. Synthesis of the corresponding Schiff-base is made in the presence of a solvent, which needs to be removed once the reaction is finished.

Thus, it is an object of the invention to provide process for making reaction product between an amine containing product and an active aldehyde or ketone in a simple one step process, thereby avoiding subsequent purification step.

It is also an object of the invention to provide a reaction process which is gentle to the active ingredients.

It is a further object of the invention to provide a reaction process which is suitable for producing industrial quantities.

Accordingly, it is a further object of the invention to provide a composition comprising a component which provides a fresh fragrance and is substantive to the treated surface.

It has now been found that the use of a low reaction temperature fulfills these needs.

SUMMARY OF THE INVENTION

The present invention is a process for producing an amine reaction product from an amine containing compound capable of reacting with an active ketone and/or aldehyde and said active ketone or aldehyde, which comprises the steps of:

a)—contacting said amine and said active, in the absence of solvent and/or drying agent, to form a reaction mixture, b)—optionally recovering the amine reaction product from said mixture, and characterised in that said contacting step a) is conducted at a temperature range of from 5 to 80° C.

In a preferred embodiment of the invention, the obtained amine reaction product is processed to form a particle, preferably a coated particle.

In another aspect of the invention, the obtained amine reaction product or particle is incorporated in a finished composition.

DETAILED DESCRIPTION OF THE INVENTION

Starting Materials

1)—Amine Reaction Product

The amine reaction product for use herein is a product of reaction between a compound containing a primary amine functional group and/or secondary amine functional group and an active ketone or aldehyde containing component, so called hereinafter "amine reaction product".

A typical disclosure of amine reaction product suitable for use herein can be found in recently filed applications EP 98870227.0, EP 98870226.2, EP 99870026.4, and EP 99870025.6, all incorporated herein by reference.

A—Primary Amine and/or Secondary Amine

By "primary and/or secondary amine", it is meant a component which carries at least one primary and/or secondary amine and/or amide function.

Of course, one amine compound may carry both primary and secondary amine compound, thereby enabling the reaction with several aldehydes and/or ketones.

Preferably, the primary amine and/or secondary amine compound is also characterized by an Odour Intensity Index of less than that of a 1% solution of methylanthranilate in dipropylene glycol.

Odour Intensity Index method

By Odour Intensity Index, it meant that the pure chemicals were diluted at 1% in Dipropylene Glycol, odor-free solvent used in perfumery. This percentage is more representative of usage levels. Smelling strips, or so called "blotters", were dipped and presented to the expert panellist for evaluation. Expert panellists are assessors trained for at least six months in odor grading and whose gradings are checked for accuracy and reproducibility versus a reference on an on-going basis. For each amine compound, the panellist was presented two blotters: one reference (Me Anthranilate, unknown from the panellist) and the sample. The panellist was asked to rank both smelling strips on the 0–5 odor intensity scale, 0 being no odor detected, 5 being very strong odor present.

Results:

The following represents Odour Intensity Index of an amine compound suitable for use in the present invention and according to the above procedure. In each case, numbers are arithmetic averages among 5 expert panellists and the results are statistically significantly different at 95% confidence level:

| | |
|---|---|
| Methylanthranilate 1% (reference) | 3.4 |
| Ethyl-4-aminobenzoate (EAB) 1% | 0.9 |

A general structure for the primary amine compound of the invention is as follows:

B—(NH2)$_n$;

wherein B is a carrier material, and n is an index of value of at least 1.

Compounds containing a secondary amine group have a structure similar to the above excepted that the compound comprises one or more —NH— groups instead of —NH2. Further, the compound structure may also have one or more of both —NH2 and —NH— groups.

Preferred B carriers are inorganic or organic carriers.

By "inorganic carrier", it is meant carrier which are non—or substantially non carbon based backbones.

Preferred primary and/or secondary amines, among the inorganic carriers, are those selected from mono or polymers or organic-organosilicon copolymers of amino derivatised organo silane, siloxane, silazane, alumane, aluminum siloxane, or aluminum silicate compounds. Typical examples of such carriers are: organosiloxanes with at least one primary amine moiety like the diaminoalkylsiloxane [H2NCH2(CH3)2Si]O, or the organoaminosilane (C6H5) 3SiNH2 described in: Chemistry and Technology of Silicone, W. Noll, Academic Press Inc. 1998, London, pp 209, 106).

Preferred primary and/or secondary amines, among the organic carriers, are those selected from aminoaryl derivatives, polyamines, amino acids and derivatives thereof, substituted amines and amides, glucamines, dendrimers, polyvinylamines and derivatives thereof, and/or copolymer thereof, alkylene polyamine, polyaminoacid and copolymer thereof, cross-linked polyaminoacids, amino substituted polyvinylalcohol, polyoxyethylene bis amine or bis aminoalkyl, aminoalkyl piperazine and derivatives thereof, bis (amino alkyl) alkyl diamine linear or branched, and mixtures thereof.

Preferred aminoaryl derivatives are the amino-benzene derivatives including the alkyl esters of 4-amino benzoate compounds, and more preferably selected from ethyl-4-amino benzoate, phenylethyl-4-aminobenzoate, phenyl-4-aminobenzoate, 4-amino-N'-(3-aminopropyl)-benzamide, and mixtures thereof.

Polyamines suitable for use in the present invention are polyethyleneimines polymers, poly[oxy(methyl-1,2-ethanediyl)], α-(2-aminomethylethyl)-ω-(2-aminomethylethoxy)-(=C.A.S No. 9046-10-0); poly[oxy(methyl-1,2-ethanediyl)], α-hydro-)-ω-(2-aminomethylethoxy)-, ether with 2-ethyl-2-(hydroxymethyl)-1,3-propanediol (=C.A.S. No. 39423-51-3); commercially available under the tradename Jeffamines T-403, D-230, D-400, D-2000; 2,2',2"-triaminotriethylamine; 2,2'-diamino-diethylamine; 3,3'-diamino-dipropylamine, 1,3 bis aminoethyl-cyclohexane commercially available from Mitsubishi and the C12 Stemamines commercially available from Clariant like the C12 Stemamin(propylenamine)$_n$ with n=¾, and mixtures thereof. Preferred polyamines are polyethyleneimines commercially available under the tradename Lupasol like Lupasol FG (MW 800), G20wfv (MW 1300), PR8515 (MW 2000), WF (MW 25000), FC (MW 800), G20 (MW 1300), G35 (MW 1200), G100 (MW 2000), HF (MW 25000), P (MW 750000), PS (MW 750000), SK (MW 2000000), SNA (MW 1000000).

Preferred amino acids for use herein are selected from tyrosine, tryptophane, lysine, glutamic acid, glutamine, aspartic acid, arginine, asparagine, phenylalanine, proline, glycine, serine, histidine, threonine, methionine, and mixture thereof, most preferably selected from tyrosine, tryptophane, and mixture thereof. Preferred amino acid derivatives are selected from tyrosine ethylate, glycine methylate, tryptophane ethylate, and mixture thereof.

Preferred substituted amines and amides for use herein are selected from nipecotamide, N-coco-1,3-propenediamine; N-oleyl-1,3-propenediamine; N-(tallow alkyl)-1,3-propenediamine; 1,4-diamino cyclohexane; 1,2-diamino-cyclohexane; 1,12-diaminododecane, and mixtures thereof.

Other primary amine compounds suitable for use herein are the glucamines, preferably selected from 2,3,4,5,6-pentamethoxy-glucamine; 6-acetylglucamine, glucamine, and mixture thereof.

Also preferred compounds are the polyethylenimine and/or polypropylenimine dendrimers and the commercially available Starburst® polyamidoamines (PAMAM) dendrimers, generation G0–G10 from Dendritech and the dendrimers Astromols®, generation 1-5 from DSM being DiAminoButane PolyAmine DAB (PA)$_x$ dendrimers with x=2$^n$×4 and n being generally comprised between 0 and 4.

Polyamino acid is one suitable and preferred class of amino-functional polymer. Polyaminoacids are compounds which are made up of amino acids or chemically modified amino acids. They can contain alanine, serine, aspartic acid, arginine, valine, threonine, glutamic acid, leucine, cysteine, histidine, lysine, isoleucine, tyrosine, asparagine, methionine, proline, tryptophan, phenylalanine, glutamine, glycine or mixtures thereof. In chemically modified amino acids, the amine or acidic function of the amino acid has reacted with a chemical reagent. This is often done to protect these chemical amine and acid functions of the amino acid in a subsequent reaction or to give special properties to the amino acids, like improved solubility. Examples of such chemical modifications are benzyloxycarbonyl, aminobutyric acid, butyl ester, pyroglutamic acid. More examples of common modifications of amino acids and small amino acid fragments can be found in the Bachem, 1996, Peptides and Biochemicals Catalog.

Preferred polyamino acids are polylysines, polyarginine, polyglutamine, polyasparagine, polyhistidine, polytryptophane or mixtures thereof. Most preferred are polylysines or polyamino acids where more than 50% of the amino acids are lysine, since the primary amine function in the side chain of the lysine is the most reactive amine of all amino acids.

The preferred polyamino acid has a molecular weight of 500 to 10.000.000, more preferably between 5.000 and 750.000.

The polyamino acid can be cross linked. The cross linking can be obtained for example by condensation of the amine group in the side chain of the amino acid like lysine with the carboxyl function on the amino acid or with protein cross linkers like PEG derivatives. The cross linked polyamino acids still need to have free primary and/or secondary amino groups left for reaction with the active ingredient.

The preferred cross linked polyamino acid has a molecular weight of 20.000 to 10.000.000, more preferably between 200.000 and 2.000.000.

The polyamino acid or the amino acid can be co-polymerized with other reagents like for instance with acids, amides, acyl chlorides. More specifically with aminocaproic acid, adipic acid, ethylhexanoic acid, caprolactam or mixture thereof. The molar ratio used in these copolymers ranges from 1:1 (reagent/amino acid (lysine)) to 1:20, more preferably from 1:1 to 1:10.

The polyamino acid like polylysine can also be partially ethoxylated.

Examples and supply of polyaminoacids containing lysine, arginine, glutamine, asparagine are given in the Bachem 1996, Peptides and Biochemicals catalog.

The polyaminoacid can be obtained before reaction with the active ingredient, under a salt form. For example polylysine can be supplied as polylysine hydrobromide. Polylysine hydrobromide is commercially available from Sigma, Applichem, Bachem and Fluka.

Examples of suitable amino functional polymers containing at least one primary and/or secondary amine group for the purpose of the present invention are:

Polyvinylamine with a MW of about 300–2.10E6;
Polyvinylamine alkoxylated with a MW of about 600, 1200 or 3000 and an ethoxylation degree of 0.5;
Polyvinylamine vinylalcohol—molar ratio 2:1, polyvinylaminevinylformamide—molar ratio 1:2 and polyvinylamine vinylformamide-molar ratio 2:1;
Triethylenetetramine, diethylenetriamine, tetraethylenepentamine;
Bis-aminopropylpiperazine;
Polyamino acid (L-lysine/lauric acid in a molar ratio of 10/1), Polyamino acid (L-lysine/aminocaproic acid/adipic acid in a molar ratio of 5/5/1), ), Polyamino acid (L-lysine/aminocaproic acid/ethylhexanoic acid in a molar ratio of 5/3/1) Polyamino acid (polylysine-cocaprolactam); Polylysine; Polylysine hydrobromide; cross-linked polylysine;
amino substituted polyvinylalcohol with a MW ranging from 400–300,000;
polyoxyethylene bis [amine] available from e.g. Sigma;
polyoxyethylene bis [6-aminohexyl] available from e.g. Sigma;
N,N'-bis-(3-aminopropyl)-1,3-propanediamine linear or branched (TPTA); and
1,4-bis-(3-aminopropyl) piperazine (BNPP).

The more preferred compounds are selected from ethyl-4-amino benzoate, polyethyleneimine polymers commercially available under the tradename Lupasol like Lupasol FG, G20, wfv, PR8515, WF, FC, G20, G35, G100, HF, P, PS, SK, SNA; the diaminobutane dendrimers Astramol®, polylysine, cross-linked polylysine, N,N'-bis-(3-aminopropyl)-1, 3-propanediamine linear or branched; 1,4-bis-( 3-aminopropyl) piperazine, and mixtures thereof. Even most preferred compounds are those selected from ethyl-4-amino benzoate, polyethyleneimine polymers commercially available under the tradename Lupasol like Lupasol FG, G20, wfv, PR8515, WF, FC, G20, G35, G100, HF, P, PS, SK, SNA; polylysine, cross-linked polylysine, N,N'-bis-(3-aminopropyl)-1,3-propanediamine linear or branched, 1,4-bis-(3-aminopropyl) piperazine, and mixtures thereof.

Advantageously, such most preferred primary and/or secondary amine compounds also provide fabric appearance benefit, in particular colour appearance benefit, thus providing a resulting amine reaction product with the dual properties of both fabric appearance benefit and delayed release of the active. Further, when the primary and/or secondary amine compound has more than one free primary and/or secondary amine group, several different active ingredients (aldehyde and/or ketone) can be linked to the amine compound.

B—Active Ketone and/or Aldehyde

Preferably, for the above mentioned compounds, by active ketone or active aldehyde, it is meant any chain containing at least 1 carbon atom, preferably at least 5 carbon atoms.

Preferably, the active ketone or active aldehyde is respectively selected from a flavour ketone or aldehyde ingredient, a pharmaceutical ketone or aldehyde active, a biocontrol ketone or aldehyde agent, a perfume ketone or aldehyde component and mixtures thereof; most preferably a perfume ketone and/or aldehyde.

Flavour ingredients include spices, flavor enhancers that contribute to the overall flavour perception.

Pharmaceutical actives include drugs.

Biocontrol agents include biocides, antimicrobials, bactericides, fungicides, algaecides, mildewcides, disinfectants, sanitiser like bleach, antiseptics, insecticides, insect and/or moth repellant, vermicides, plant growth hormones.

Typical antimicrobials include Glutaraldehyde, Cinnamaldehyde, and mixtures thereof. Typical insect and/or moth repellants are perfume ingredients, such as citronellal, citral, N,N diethyl meta toluamide, Rotundial, 8-acetoxycarvotanacenone, and mixtures thereof. Other examples of insect and/or moth repellant for use herein are disclosed in U.S. Pat. Nos. 4,449,987, 4,693,890, 4,696,676, 4,933,371, 5,030,660, 5,196,200, and "Semio Activity of Flavor and Fragrance molecules on various Insect Species", B. D. Mookherjee et al., published in *Bioactive Volatile Compounds from Plants*, ASC Symposium Series 525, R. Teranishi, R. G. Buttery, and H. Sugisawa, 1993, pp. 35–48.

A typical disclosure of suitable ketone and/or aldehydes, traditionally used in perfumery, can be found in "perfume and Flavor Chemicals", Vol. I and II, S. Arctander, Allured Publishing, 1994, ISBN 0-931710-35-5.

Perfume ketones components include components having odoriferous properties.

Preferably, for the above mentioned compounds, the perfume ketone is selected from buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-Ionone, Beta-Ionone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbornane, 6,7-Dihydro-1,1,2,3,3-Pentamethyl-4(5H)-Indanone, 4-Damascol, Dulcinyl or Cassione, Gelsone, Hexalon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, Tetrameran, hedione, and mixtures thereof.

More preferably, for the above mentioned compounds, the preferred ketones are selected from Alpha Damascone, Delta Damascone, Iso Damascone, Carvone, Gamma-Methyl-Ionone, Iso-E-Super, 2,4,4,7-Tetramethyl-oct-6-en-3-one, Benzyl Acetone, Beta Damascone, Damascenone, methyl dihydrojasmonate, methyl cedrylone, hedione, and mixtures thereof.

Perfume aldehyde components include components having odoriferous properties.

Preferably, for the above mentioned compounds, the perfume aldehyde is selected from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl) oxy] acetaldehyde, 4-isopropylbenzyaldehyde, 1,2,3,4,5,6, 7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carboxaldehyde, 5 or 6 methoxy0hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, para-tolylacetaldehyde; 4-methylphenylacetaldehyde, 2-methyl-4-(2,6,6-trimethyl-1-cyclohexen-1-yl)-2-butenal, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl) benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, 1-p-menthene-q-carboxaldehyde, citral, lilial and mixtures thereof.

Most preferred aldehydes are selected from citral, 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P.T. Bucinal, lyral, cymal, methyl nonyl acetaldehyde, trans-2-nonenal, lilial, trans-2-nonenal, and mixture thereof.

In the above list of perfume ingredients, some are commercial names conventionally known to one skilled in the art, and also includes isomers. Such isomers are also suitable for use in the present invention.

In another embodiment, especially suitable for the purpose of the present invention are the perfume compounds, preferably the perfume ketones or aldehydes, characterised by having a low Odor Detection Threshold. Such Odor Detection Threshold (ODT) should be lower than 1 ppm, preferably lower than 10 ppb—measured at controlled Gas Chromatography (GC) conditions such as described here below. This parameter refers to the value commonly used in the perfumery arts and which is the lowest concentration at which significant detection takes place that some odorous material is present, as referred to for example in "Compilation of Odor and Taste Threshold Value Data (ASTM DS 48 A)", edited by F. A. Fazzalari, International Business Machines, Hopwell Junction, N.Y. and in Calkin et al., Perfumery, Practice and Principles, John Willey & Sons, Inc., page 243 et seq (1994). For the purpose of the present invention, the Odor Detection Threshold is measured according to the following method:

The gas chromatograph is characterized to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 0.02 minutes, the sampled volume is calculated. Since the precise concentration at the detector at any point in time is known, the mass per volume inhaled is known and hence the concentration of material. To determine the ODT of a perfume material, solutions are delivered to the sniff port at the back-calculated concentration. A panelist sniffs the GC effluent and identifies the retention time when odor is noticed. The average over all panelists determines the threshold of noticeability. The necessary amount of analyte is injected onto the column to achieve a certain concentration, such as 10 ppb, at the detector. Typical gas chromatograph parameters for determining odor detection thresholds are listed below.

GC: 5890 Series II with FID detector
7673 Autosampler
Column: J&W Scientific DB-1
Length 30 meters ID 0.25 mm film thickness 1 micron
Method:
Split Injection: 17/1 split ratio
Autosampler: 1.13 microliters per injection
Column Flow: 1.10 mL/minute
Air Flow: 345 mL/minute
Inlet Temp. 245° C.
Detector Temp. 285° C.
Temperature Information
Initial Temperature: 50° C.
Rate: 5 C./minute
Final Temperature: 280° C.
Final Time: 6 minutes
Leading assumptions: 0.02 minutes per sniff
GC air adds to sample dilution Examples of such preferred perfume components are those selected from: 2-methyl-2-(para-iso-propylphenyl)-propionaldehyde, 1-(2,6,6-trimethyl-2-cyclohexan-1-yl)2-buten-1-one and/or para-methoxy-acetophenone. Even more preferred are the following compounds having an ODT≦10 ppb measured with the method described above: undecylenic aldehyde, undecalactone gamma, heliotropin, dodecalactone gamma, p-anisic aldehyde, para hydroxy-phenyl-butanone, cymal, benzyl acetone, ionone alpha, p.t.bucinal, damascenone, ionone beta and methyl-nonyl ketone.

Typically the level of active is of from 10 to 90%, preferably from 30 to 85%, more preferably from 45 to 80% by weight of the amine reaction product.

2)—Synthesis of the Amine Reaction Product

Synthesis of the amine reaction product is made as follows;

First, the amine and the active are contacted together, in the absence of solvent, to form a reaction mixture. Contacting of the amine and the active involves slow stirring, so that intimate contact between the reactants is obtained. The stirring may take place in a reaction vessel like a rotavapor apparatus, or Grignard distillation apparatus. Depending on the quantities which are required, the material of the apparatus will vary. Hence, for small quantities below 50 liter, the apparatus is made of glass, whereas for bigger quantities like for apparatus of 50 to 5000 liters, it is made of steel or enamel metal. When use of a reaction vessel having an outlet for the reactants and an outlet for the reaction product, one will need to ensure that the diameter of the outlet for the reaction mixture product is sufficiently large to permit a good flow. For example, for a 1 kg batch, the outlet for the reaction products is 3 cm. To further improve the flow, the outlet and/or apparatus may be heated to 50–60 C. to decrease the viscosity of the resulting product.

By slow stirring, it is meant a stirring intensity of from 20 to 100 rpm. Of course, this intensity will also depends on the diameter of the apparatus and/or the quantities to stir; i.e. the more quantity of reactant being present and/or the higher the diameter of the apparatus, the higher stirring intensity will be needed. Further, the addition of spinning balls to the mixture will improve the homogeneity of the mixture.

As for the stirring intensity, the time of mixing will also depend on the quantity of reactant being present and/or the higher the diameter of the apparatus. Still, a typical mixing time is of from 10 minutes to up to 4 hours, preferably of from 20 minutes to 4 hours.

One essential feature of the invention is that the contacting step is conducted at a temperature range of from 5° C. to 80° C., preferably of from 15° C. to 60° C., more preferably of from 18° C. to 50° C., and most preferably is of 40° C. Such low reaction temperature results in less required heating which enable a more economical process. Further, the use of these low temperature enable less by-product like Schiff-bases polymerisation products, thereby giving resulting amine reaction product with higher purity.

Preferably, the reaction mixture has a substantially constant temperature. By substantially constant, it is meant that the temperature should not deviate by more than 10° C. from its set original value. Indeed, the reaction may sometimes be exothermic, which abrupt temperature increases may cause degradation of the active ingredient. Accordingly, it is preferred to control the temperature of reaction by means of cooling means like water bath, or cold water condenser well known in the art. Still, freezing fluid may also be used as cooling means. The cooling means are often necessary when the amine compound and the aldehyde and/or ketone are added together.

Preferably, the water which is formed from the reaction between the amine compound and the aldehyde is removed throughout the reaction. This is easily achieved by means of a vacuum pump which is efficient enough to remove the water at 40° C. One can also use a mechanical pump like a "Leybold Triviac" but which is protected by a carbonic ice trap. With a water pump, the water which is formed from the reaction is removed. The reaction is then better driven and its rate is accelerated.

For amine containing compound which are supplied in aqueous form, like for example the commercial Lupasol samples which contain up to 50% by weight of water, it is then preferred for industrial processes to remove the water throughout the process reaction or at the end of the process reaction.

Still another advantage of the use of the vacuum pump is the control of the bubbles and resulting foam formation. Bubbles and foam are not desired for the process of the invention as this tends to give spilling and so lost of the product. Not to be bound by theory, it is believed that this phenomena arises due to the use of the Lupasol polymers as well as to the pumping step. Accordingly, it has been found that by modulating the vacuum within the reaction vessel the formation of bubbles and foam which may arises during the reaction is controlled thereby avoiding the development of foam.

Advantageously, the process reaction is free of optional drying agent like anhydrous $Na_2SO_4$, $CaCl_2$, molecular sieves, $P_2O_5$.

Once the amine reaction product is formed, it is optionally recovered from the reaction mixture when the yield turns out to be low. However, most of the time, the yields obtained far exceed 90% by weight, and preferably are of at least 98%, which enable the product to be used as is, i.e. no additional recovery is required.

Accordingly, there is provided the amine reaction product as obtainable by this process.

Preferred amine reaction products are those which have a Dry Surface Odour Index as per given in co-pending application EP 98870155.3 given at page 29, line 26 to page 32 line 29, in which the specified unperfumed base for fabric sufaces and hard surfaces are respectively as follow:

| | % by weight |
|---|---|
| Composition for fabric surface test | |
| LAS | 16 |
| NaSKS-6 | 6 |
| PB1 | 8 |
| TAED | 2.4 |
| Carbonate | 1 |
| Sodium Carbonate | 1 |
| HEDP | 0.4 |
| SRP1 | 0.2 |
| Photobleach | 0.013 |
| Citric acid | 1.0 |
| Protease | 0.3 |
| Lipase | 0.1 |
| Cellulase | 0.1 |
| Amylase | 0.3 |
| Zeolite | 3.0 |
| TFAA | 3.0 |
| QAS1 | 2.5 |
| Silicone antifoam | 1.0 |
| Misc/minors to balance to 100% | |
| Composition for hard surface test | |
| C12–14 EO 21 | 2 |
| C12–14 EO 5 | 2.5 |
| C9–11 EO 5 | 2.5 |
| LAS | 0.8 |
| Na2CO3 | 0.2 |
| Citric acid | 0.8 |
| Caustic acid | 0.5 |
| Fatty acid | 0.5 |
| SCS | 1.5 |
| Water &Misc/Minors to balance to 100% | |

Most preferred amine reaction products are those resulting from the reaction of polyethyleneimine polymer like Lupasol polymers, BNPP, or TPTA with one or more of the following Alpha Damascone, Delta Damascone, Carvone, Gamma-Methyl-lonone, Hedione, Florhydral, Lilial, Heliotropine, and 2,4-dimethyl-3-cyclohexen-1-carboxaldehyde. Still other preferred amine reaction products are those resulting from the reaction of Astramol Dendrimers with Carvone as well as those resulting from the reaction of ethyl-4-amino benzoate with one or more of the following 2,4-dimethyl-3-cyclohexen-1-carboxaldehyde, and trans-2-nonenal. Still another preferred amine reaction products are those resulting from the reaction of polylysine with one or more of the following Alpha Damascone, Delta Damascone, Carvone, and 2,4-dimethyl-3-cyclohexen-1-carboxaldehyde.

Even most preferred amine reaction products are those from the reaction of Lupasol HF with Delta Damascone; LupasolG35 with Alpha Damascone; LupasolG100 with 2,4-dimethyl-3-cyclohexen-1-carboxaldehyde, BNPP or TPTA with Alpha and Delta Damascone; ethyl-4-amino benzoate with 2,4-dimethyl-3-cyclohexen-1-carboxaldehyde.

Most preferred amine reaction products are those fulfilling the Dry Surface Odor Index as per given in co-pending application EP 98870155.3 given at page 29, line 26 to page 32 line 29.

The resulting amine reaction product may then be used as is like by spray-on application or processed for ease of handling into fully-formulated composition.

Carrier

For ease of incorporation into finished product, it is preferred that the amine reaction product is processed with a carrier.

Suitable carrier for use herein are selected from carrier having a melting point of from less than 30° C., from 30° C. to 135° C., acidic carrier, and mixtures thereof.

a)—Carrier Having a Melting Point of from 30° C. to 135° C.

Typical of carrier which can be use herein are the carrier having a melting point between 30° C. and 135° C., preferably between 45° C. and 85° C. By means of this carrier, particles of amine reaction product will be produced.

Suitable carrier for use in the process invention are components like organic polymeric compounds, waxes, paraffins, oils, glycerides, monoglycerides, diglycerides, triglycerides, fatty acids, anionic surfactants; nonionic surfactants, cationic surfactants, zwitterionic surfactants, and mixtures thereof, preferably selected from organic polymeric compound, nonionic surfactants, and mixtures thereof.

Preferred organic polymeric compounds suitable for mixing with primary amine compound herein include polyethylene glycols, and derivatives thereof, particularly those of molecular weight 1000–10000, more particularly 2000 to 8000 and most preferably about 4000.

Essentially any nonionic surfactants useful for detersive purposes can be included in the compositions provided it has a melting point between 30° C. and 135° C.

Exemplary, non-limiting classes of useful nonionic surfactants are listed below.

Nonionic Polyhydroxy Fatty Acid Amide Surfactant

Polyhydroxy fatty acid amides suitable for use herein are those having the structural formula R2CONR1Z wherein: R1 is H, $C_1$–$C_4$ hydrocarbyl, 2-hydroxy ethyl, 2-hydroxy propyl, or a mixture thereof, preferable $C_1$–$C_4$ alkyl, more preferably $C_1$ or $C_2$ alkyl, most preferably $C_1$ alkyl (i.e., methyl); and R2 is a $C_5$–$C_{31}$ hydrocarbyl, preferably straight-chain $C_5$–$C_{19}$ alkyl or alkenyl, more preferably straight-chain $C_9$–$C_{17}$ alkyl or alkenyl, most preferably straight-chain $C_{11}$–$C_{17}$ alkyl or alkenyl, or mixture thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl.

Nonionic Condensates of Alkyl Phenols

The polyethylene, polypropylene, and polybutylene oxide condensates of alkyl phenols are suitable for use herein. In general, the polyethylene oxide condensates are preferred. These compounds include the condensation products of alkyl phenols having an alkyl group containing from about 6 to about 18 carbon atoms in either a straight chain or branched chain configuration with the alkylene oxide with from about 1 to about 150 moles of alkylene oxide per mole of alcohol.

Nonionic Ethoxylated Alcohol Surfactant

The alkyl ethoxylate condensation products of aliphatic alcohols with from about 1 to about 150 moles of ethylene oxide are suitable for use herein. The alkyl chain of the aliphatic alcohol can either be straight or branched, primary or secondary, and generally contains from 6 to 22 carbon atoms. Particularly preferred are the condensation products of alcohols having an alkyl group containing from 8 to 20 carbon atoms with from about 25 to about 150 moles of ethylene oxide per mole of alcohol, preferably 50 to 100, more preferably 80 moles of ethylene oxide per mole of alcohol.

Preferred nonionic ethoxylated alcohol surfactants are selected from tallow ($C_{16}$–$C_{18}$) alcohol ethoxylated with 25, 50, 80, or 100 moles of ethylene oxide commercially available from under the tradename of Lutensol from BASF, Empilan from Albright and Wilson, and Genapol from Clariant. The most preferred nonionic ethoxylated alcohol surfactant is tallow ($C_{16}$–$C_{18}$) alcohol ethoxylated with 80 moles of ethylene oxide and commercially available under the tradename of Lutensol 80/80 from BASF, Empilan KM 80 from Albright and Wilson, or Genapol T800 from Clariant.

Nonionic Ethoxylated/Propoxylated Fatty Alcohol Surfactant

The ethoxylated $C_6$–$C_{22}$ fatty alcohols and $C_6$–$C_{22}$ mixed ethoxylated/propoxylated fatty alcohols are suitable surfactants for use herein, particularly where water soluble. Preferably the ethoxylated fatty alcohols are the $C_{10}$–$C_{22}$ ethoxylated fatty alcohols with a degree of ethoxylation of from 25 to 150, most preferably these are the $C_{12}$–$C_{18}$ ethoxylated fatty alcohols with a degree of ethoxylation from 50 to 80. Preferably the mixed ethoxylated/propoxylated fatty alcohols have an alkyl chain length of from 10 to 18 carbon atoms, a degree of ethoxylation of from 3 to 30 and a degree of propoxylation of from 1 to 30.

Nonionic EO/PO Condensates with Propylene Glycol

The condensation products of ethylene oxide with a hydrophobic base formed by the condensation of propylene oxide with propylene glycol are suitable for use herein. The hydrophobic portion of these compounds preferably has a molecular weight of from about 1500 to about 1800 and exhibits water insolubility. Examples of compounds of this type include certain of the commercially-available Pluronic™ surfactants, marketed by BASF.

Nonionic EO Condensation Products with Propylene Oxide/Ethylene Diamine Adducts

The condensation products of ethylene oxide with the product resulting from the reaction of propylene oxide and ethylenediamine are suitable for use herein. The hydrophobic moiety of these products consists of the reaction product of ethylenediamine and excess propylene oxide, and generally has a molecular weight of from about 2500 to about 3000. Examples of this type of nonionic surfactant include certain of the commercially available Tetronic™ compounds, marketed by BASF.

Nonionic Alkylpolysaccharide Surfactant

Suitable alkylpolysaccharides for use herein are disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6- positions on the preceding saccharide units.

The preferred alkylpolyglycosides have the formula

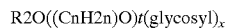
$R_2O((C_nH_{2n})O)_t(\text{glycosyl})_x$ wherein R2 is selected from the group consisting of alkyl, alkylphenyl, hydroxyalkyl, hydroxyalkylphenyl, and mixtures thereof in which the alkyl groups contain from 10 to 18, preferably from 12 to 14, carbon atoms; n is 2 or 3; t is from 0 to 10, preferably 0, and X is from 1.3 to 8, preferably from 1.3 to 3, most preferably from 1.3 to 2.7. The glycosyl is preferably derived from glucose.

Nonionic Fatty Acid Amide Surfactant

Fatty acid amide surfactants suitable for use herein are those having the formula: $R^6CON(R^7)_2$ wherein $R^6$ is an alkyl group containing from 7 to 21, preferably from 9 to 17 carbon atoms and each $R^7$ is selected from the group consisting of hydrogen, $C_1$–$C_4$ alkyl, $C_1$–$C_4$ hydroxyalkyl, and —$(C_2H_4O)_xH$, where x is in the range of from 1 to 3.

Preferred carrier materials are selected from nonionic ethoxylated alcohol surfactants.

Processing of the amine reaction product with the carrier is done by thoroughly mixing the amine reaction product with the carrier. Advantageously, there is no need for additional ingredients to provide a resulting substantially homogenous mixture. This mixing is done at the lowest possible temperature, i.e. just above the melting point of the carrier. The mixing step is carried out until a complete homogeneous mixture is obtained. By "homogeneous", it is meant compositions which have similar appearance to the resulting composition of a 20 g of amine reaction product mixed with 80 g of TAE80 for 5 minutes by means of an Ultra Turrax, the temperature of mixing being of about 70° C.

b)—Carrier Having a Melting Point of from Less than 30° C.

Still other type of carrier are the carrier having a melting point below 30° C., preferably of from minus 150° C. to less than 30° C. Typical of such carrier includes liquid as well as solid carrier material. The liquid carrier can be in any suitable physical form like hydrophobic or hydrophilic form.

As used herein in relation to carrier materials, "hydrophobic" means substantially water insoluble; "hydrophilic" means substantially water soluble. In this regard, "substantially water insoluble" shall refer to a material that is not soluble in distilled (or equivalent) water, at 25.degree. C., at a concentration of 0.2% by weight, and preferably not soluble at 0.1% by weight (calculated on a water plus carrier weight basis). "Substantially water soluble" shall refer to a material that is soluble in distilled (or equivalent) water, at 25.degree. C., at a concentration of 0.2% by weight, and are preferably soluble at 1.0% by weight. The terms "soluble", "solubility" and the like, for purposes hereof, corresponds to the maximum concentration of carrier, as applicable, that can dissolve in water or other solvents to form a homogeneous solution, as is well understood to those skilled in the art.

Typical of materials that are in hydrophobic form include ingredients useful in perfumery. Typical of such ingredients are the perfume raw materials, solvents, and mixtures thereof. Typical hydrophobic raw materials include the ketones or aldehydes like hexyl cinnamic aldehyde, hydrocarbons like Limolene, d-Limonene, esters like Hercolyn D, benzyl salicylate, hexyl salicylate, triethyl citrate, isopropyl myristate, or mixtures thereof, or hydrophobic perfume composition preferably incorporating one or more of these raw materials.

Typical hydrophobic solvents include diethyl phtalate, ethers like butoxypropoxypropanol, and mixtures thereof.

Also suitable for use herein are the finished perfume compositions which have hydrophobic properties.

Typical of materials that are in hydrophilic form include alcohols like methanol, ethanol, dipropyleneglycol, water, nonionic surfactants as above described but having a melting point below 30 C, or mixtures thereof.

Preferred carrier materials are selected from benzyl salicylate, diethyl phthalate, dipropylene glycol, methanol, ethanol, and mixtures thereof.

c)—Acid carrier

Still another type of carrier suitable for use herein is the direct mixing of the amine reaction product with an acid carrier, thereby resulting in already formed agglomerates.

By "acid carrier", it is meant a carrier which forms a salt with the amine reaction product. Not to be bound by theory, it is believed that the salt formation occurs by reacting the amine reaction product with an acid. The salt formation takes place via a reaction of the acid at the nitrogen of the β-aminoketone or imine function. Still, the salt formation may also take place at other nucleophilic centers of the amine or amine reaction product.

Typical of these acid carrier for use herein are the commonly known organic acids or inorganic acids, which fall under the description of Bronsted or Lewis acids.

Definition of an acid can be found in March J., Advanced Organic Chemistry, Chapter 8, page 248 for definition of a Bronsted acid and page 260 for the definition of a Lewis acid, John Wiley&Sons, New York, 1992.

Suitable acid carrier for use herein have a pKa relative to water of from minus 9 to 16, more preferably from minus 2 to 10, most preferably from 0 to 7. For example, alcohols like phenol derivatives are suitable acid carrier for use herein. A typical example of such phenol derivative is picric acid which has a pKa of 0.25.

Preferred organic or inorganic acids include those conventionally known as solid binders or agglomerating agents. More preferred organic acids are substantially water soluble solid binders or agglomerating agents. Most preferred are organic acids used in detergent applications, for example as builders.

"Substantially water soluble" shall refer to a material that is soluble in distilled (or equivalent) water, at 25° C., at a concentration of 0.2% by weight, and are preferably soluble at 1.0% by weight.

A "solid" is defined as a material that is a solid at ambient temperatures, and so solid substantially water-soluble binder or agglomerating agent must have a melting point of at least 30° C., and preferably of at least 40° C.

Suitable water-soluble binders or agglomerating agents as organic acid carriers include monocarboxylic acids, monomeric polycarboxylic acids, homo or copolymeric polycarboxylic acids, inorganic acids, and mixtures thereof.

Suitable example of monocarboxylic acids containing one carboxy group include formic acid, acetic acid, propionic acid, butyric acid, valeric acid, caproic acid, enanthic acid, caprylic acid, pelargonic acid, capric acid, lauric acid, myristic acid, palmitic acid, stearic acid, and mixtures thereof.

Still other suitable monocarboxylic acids are the monocarboxylic acids substituted by any of the following groups: CH3—(CH2)$_n$, wherein n is an integer of value of at least 1, CH3, OH, NH2, Cl, Br, F, I, OR", NHR", NR"2, NO2, SO3, cyclic rings like cyclopentane, cyclohexane, phenyl, benzyl, or a mixture of these substituents; wherein R" is selected from saturated or unsaturated alkyl chains. Preferred examples are 1-methylcyclohexanecarboxylic acid, glycolic acid, mandelic acid, lactic acid, salicylic acid, benzoic acid, and derivatives thereof. The substituents may also be anywhere in the alkyl chain attached to the acidic function. The alkyl chain can be saturated or non saturated.

Still other typical of organic acids suitable for use herein as acid carrier includes the polycarboxylic acids containing two carboxy groups. Typical of these ingredients are selected from succinic acid, malonic acid, (ethylenedioxy) diacetic acid, maleic acid, diglycolic acid, tartaric acid, tartronic acid, fumaric acid, oxalic acid, glutaric acid, adipic acid, pimelic acid, suberic acid, azelaic acid, or sebacic acid, as well as the ether carboxylic acid and the sulfinyl carboxylic acids, and mixtures thereof.

Other dicarboxylic acids suitable for use herein are the dicarboxylic acids substituted by CH3—(CH2)$_n$, wherein n is an integer of value of at least 1, CH3, OH, NH2, Cl, Br, F, I, OR", NHR", NR"2, NO2, SO3, cyclic rings like cyclopentane, cyclohexane, phenyl, benzyl, or a mixture of these substituents; wherein R" is selected from saturated or unsaturated alkyl chain. Preferred examples of such substituted dicarboxylic acids are phtalic acid, isophtalic acid, terephtalic acid, malic acid, fumaric acid, tartaric acid, or mixtures thereof. The substituents may also be anywhere in the alkyl chain attached to the acidic functions. The alkyl chains can be saturated or non saturated.

Other polycarboxylic acids suitable for use herein are the polycarboxylic acids containing three carboxy groups and include, in particular, water-soluble citric acid, aconitric and citraconic acid as well as succinic derivatives such as the carboxymethyloxysuccinic described in British Patent No. 1,379,241, lactoxysuccinic described in British Patent No. 1,389,732, and aminosuccinic described in Netherlands Application 7205873, and the oxypolycarboxylic materials such as 2-oxa-1,1,3-propane tricarboxylic described in British Patent No. 1,387,447.

Other polycarboxylic acids suitable for use herein are the polycarboxylic acids containing four carboxy groups and include oxydisuccinic disclosed in British Patent No. 1,261, 829, 1,1,2,2-ethane tetracarboxylic, 1,1,3,3-propane tetracarboxylic and 1,1,2,3-propane tetracarboxylic. Polycarboxylic containing sulfo substituents include the sulfosuccinic derivatives disclosed in British Patent Nos. 1,398,421 and 1,398,422 and in U.S. Pat. No. 3,936,448, and the sulfonated pyrolysed citratic described in British Patent No. 1,439,000.

Alicyclic and heterocyclic polycarboxylic include cyclopentane-cis,cis,cis-tetracarboxylic, cyclopentadienide pentacarboxylic, 2,3,4,5-tetrahydrofuran-cis, cis, cis-tetracarboxylic, 2,5-tetrahydrofuran-cis-dicarboxylic, 2,2,5,5-tetrahydrofuran-tetracarboxylic, 1,2,3,4,5,6-hexanehexacarboxylic, polyacrylic acid, polymaleic acid, polymaleic-acrylic acids, sugar-acids like glucose-phosphonic acid, gluconic acid, glucuronic acid, mannanic acid, galactonic acid, arabinamic acid, and carboxymethyl derivatives of polyhydric alcohols such as sorbitol, mannitol and xylitol. Aromatic polycarboxylic include mellitic acid, pyromellitic acid and the phthalic acid derivatives disclosed in British Patent No. 1,425,343.

Other suitable carriers are amino acids like, glycine, lysine, alanine, valine, leucine, isoleucine, proline, phenylalanine, tyrosine, tryptophan, serine, threonine, cysteine, methionine, asparagine, glutamine, aspartate, glutamate, arginine, histidine, and mixtures thereof.

Other suitable acid carriers are the so called inorganic acids like for example HF, HCl, HBr, HI, $H_2SO_4$, $H_2SO_3$, $H_2CO_3$, $HNO_2$, $HNO_3$, $HClO_4$, $HClO_3$, $HClO_2$, $HClO$, or $H_3PO_4$, $H_4P_2O_7$, or $H_5P_3O_{10}$ or mixture thereof. Also useful herein as acid carriers are the protonated forms of the anionic surfactants, like the protonated form of the linear $C_{11-13}$ alkyl benzene sulfonate anionic surfactant.

Other suitable carriers are acid anhydrides and acyl halides. Acid anhydrides react in the presence of water to acids. Sometimes, the production of the amine reaction product is followed by the incomplete removal of the water in the amine samples. It may then be desired to remove the remaining water by reacting it with the acid anhydrides to form acids which in turn make the salt with the amine reaction product.

Other suitable carriers are acids, where the acidic proton is linked to C, N, S, Si or other non-oxygen atoms. Example of such acids is 2,4-pentanedione.

Preferably, to avoid possible hydrolysis of the amine reaction product in-situ due to the eventual additional water coming from the acid carrier, the acid carrier is used in its anhydrous forms. For example, citric acid is available under anhydrous form or as a monohydrate.

Of the above, the preferred acid carriers are polycarboxylic acids selected from citric acid, tartaric acid, malonic acid, succinic acid, oxalic acid, adipic acid, maleic acid, malic acid, phtalic acid, succinic acid, hydroxysuccinic acid, polyacrylic acid, and mixtures thereof.

Processing of the amine reaction product with the acid carrier is done by first dissolving the amine reaction product in anhydrous solvent, preferably ethanol. Separately, the acid carrier is also dissolved in the same solvent that is used for the amine reaction product. The two solutions are then slowly added together, by adding the solution of the acid carrier to the solution of the amine reaction product whilst maintaining the temperature upon the addition to room temperature. During the addition, the salt of the amine reaction product and the acid carrier precipitate resulting a solid powder. The solvent is removed by either filtering off the salt and drying or by evaporation of the solvent. Preferably the salt is obtained by filtering off.

One convenient way for making the dispersed amine reaction product in industrial quantities is via a continous process like by means of a twin Screw Extruder (TSE). Suitable TSE include the TX-57 MAG, TX-85 MAG, TX-110 MAG, TX-144 MAG, or TX-178 MAG twin screw extruder from Wenger. One preferred for use herein is the TX-57 MAG. TSE suitable for use herein comprise at one of their extremities so called herein after "first part of the TSE" two distinct inlet: one for the active and the other for the amine, and at about the middle of the TSE, so called hereinafter "second part of the TSE" another inlet for the carrier. Temperature controllers are also distributed along the TSE. One typical method involves:

In the first part of the TSE, the active brought at a temperature between 5 and 40° C. and the amine brought at a temperature between 5 and 40° C. are incorporated into the TSE via their respective inlet and mixed together at a screw speed between 50 and 200, preferably 150 rpm, to make the resulting amine reaction product. Typical weight rate of material which is introduced in the TSE are of 5 to 200 kg/hour for each of the active and of the amine. The temperature within the reaction mixture is preferably within the range of 20 to 40° C. with a residence time between 10 and 45 seconds. Thereafter, the resulting amine reaction product is brought along the TSE for dispersion into a carrier, preferably a carrier having a melting point between 30° C. and 135° C., the carrier having been previously brought to a temperature between 20 and 150° C. at a rate of between 50 and 200, preferably 150 kg/hour. The dispersion temperature at the end of the TSE was about 80° C. and the total residence time of the mixture within the TSE is preferably between 10 seconds to 2 minutes. The resulting dispersion is then collected for optional agglomeration and/or coating process as outlined thereafter.

Specifically, in the first part of the TSE, the Damascone brought at a temperature of 20° C. and Lupasol WF brought at a temperature of 20° C. are mixed at a screw speed of 150 rpm to make the resulting amine reaction product, at a weight ratio of 48 kg/hour Damascone and 32 kg/hour of Lupasol WF. In the second part of the TSE, the amine reaction product is dispersed into TAE80 brought at a temperature of 70° C. at a rate of 120 kg/hour. The total production rate was thus 200 kg/hour.

Still, an alternative process for making the amine reaction product in a carrier is by a batch process using a mixing tank in which pre—or melted therein carrier, e.g. TAE80 is placed into the mixing tank before incorporation of the amine component and subsequently of the active both incorporated at room temperature.

Typically when the amine reaction product is mixed with a carrier, the amine reaction product will be present in an amount of from 10 to 85%, preferably 20 to 80%, more preferably 45 to 75% by weight of the processed reaction product in the produced particle. In this instance, the amount of carrier will be sufficient to add up to 100%.

Of course, the resulting particle may also contain minors but in quantities which will not exceed the amount of carrier material. Hence, if desired, the processed particle may contain one or more additional ingredients like a surfactant for improved solubility or dispersability. Typical of such surfactant are the anionic, nonionic, or cationic surfactants. Preferably, the weight ratio of such additional ingredient(s) to the carrier is of up to 1:1. Typically the carrier will be present in an amount of from 5 to 90%, preferably from 15 to 80% and most preferably from 20 to 70%, by weight of the produced particles in the processed amine reaction product.

Accordingly, there is also provided a processed amine reaction product as obtainable by the process of the invention.

In a preferred marketing execution, a coating on the particle can be provided, which depending on the nature of this coating will give ease of dispersion, improved storage stability, flowability and/or improved fabric substantivity of the coated particle.

Coating Agents

When use of a carrier, as above described, and in particular with a melting point between 35 and 135° C. is made for the mixing with the amine reaction product, it is then preferred to further process the mixture to form a coated particle like e.g. by adsorption of the mixture onto a solid, preferably porous coating. The resulting coated particles can be in any form which is suitable for incorporation into liquid or powders, preferably powders, such as agglomerate, pellets, tablets, or mixtures thereof.

Suitable coating agents for both solid, including paste, and liquid mixture are substantially water-soluble solid binder or agglomerating agents such as those given above as acid carrier, i.e. water soluble organic polymeric compounds, water soluble monomeric polycarboxylates, or their acid forms, homo or copolymeric polycarboxylic acids or their salts in which the polycarboxylic acid comprises at least two carboxylic radicals separated from each other by not more that two carbon atoms, carbonates, bicarbonates, borates, phosphates, sulfate salts like sodium and magnesium sulfate, inorganic perhydrate salts including perborate like perborate monohydrate, percarbonate, silicates, starch, cyclodextrin, and mixtures of any of the foregoing. Of course, for the purpose of the invention it is preferred when a coating is provided that this is of a different nature to that of the carrier.

Suitable organic polymeric compounds suitable as coating agents include cellulose derivatives such as methylcellulose, carboxymethylcellulose, hydroxypropylcellulose and hydroxyethylcellulose, as well as carbohydrates like pectins, and gums. Further compounds are carbohydrates and derivatives such as fructose, xylose, galactose, galacturonic acid or glucose based polymers like inuline, dextran, xyloglucan, pectin or gums.

Borate, as well as builders containing borate-forming materials that can produce borate under detergent storage or wash conditions can also be used but are not preferred at wash conditions less that about 50° C., especially less than about 40° C.

Examples of carbonates are the alkaline earth and alkali metal carbonates, including sodium carbonate and sesquicarbonate and mixtures thereof with ultra-fine calcium carbonate as disclosed in German Patent Application No. 2,321,001 published on Nov. 15, 1973.

Specific examples of water-soluble phosphates are the alkali metal tripolyphosphates, sodium, potassium and ammonium pyrophosphate, sodium and potassium and ammonium pyrophosphate, sodium and potassium orthophosphate, sodium polymeta/phosphate in which the degree of polymerization ranges from about 6 to 21, and salts of phytic acid.

Suitable silicates include the water soluble sodium silicates with an $SiO_2$: $Na_2O$ ratio of from 1.0 to 2.8, with ratios of from 1.6 to 2.4 being preferred, and 2.0 ratio being most preferred. The silicates may be in the form of either the anhydrous salt or a hydrated salt. Sodium silicate with an $SiO_2$: $Na_2O$ ratio of 2.0 is the most preferred silicate.

Typical disclosure of cyclodextrin derivatives are disclosed in WO96/05358, U.S. Pat. No. 3,426,011, Parmerter et al., issued Feb. 4, 1969; U.S. Pat. Nos. 3,453,257; 3,453,258; 3,453,259; and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; all of said patents being incorporated herein by reference.

Although less preferred for use herein because of their lower solubility, partially water soluble coating agents may also be used as coating agent. These compounds are indeed less preferred because during the wash cycle the amine reaction product will still be at least partially coated and therefore can not display its full functionality of long lasting freshness on dry fabrics or hard surfaces. Examples of partially water soluble coating agents include the crystalline layered silicates. Examples of largely water insoluble builders include the sodium aluminosilicates.

Crystalline layered sodium silicates have the general formula $NaMSi_xO_{x+1}.yH_2O$ wherein M is sodium or hydrogen, x is a number from 1.9 to 4 and y is a number from 0 to 20. Crystalline layered sodium silicates of this type are disclosed in EP-A-01 64514 and methods for their preparation are disclosed in DE-A-3417649 and DE-A-3742043. For the purpose of the present invention, x in the general formula above has a value of 2, 3 or 4 and is preferably 2. The most preferred material is δ-$Na_2Si_2O_5$, available from Hoechst AG as NaSKS-6.

Suitable aluminosilicate zeolites have the unit cell formula $Na_z[(AlO_2)_z(SiO_2)_y]$. $XH_2O$ wherein z and y are at least 6; the molar ratio of z to y is from 1.0 to 0.5 and x is at least 5, preferably from 7.5 to 276, more preferably from 10 to 264. The aluminosilicate material are in hydrated form and are preferably crystalline, containing from 10% to 28%, more preferably from 18% to 22% water in bound form.

The aluminosilicate ion exchange materials can be naturally occurring materials, but are preferably synthetically derived. Synthetic crystalline aluminosilicate ion exchange materials are available under the designations Zeolite A, Zeolite B, Zeolite P, Zeolite X, Zeoilte MAP, Zeolite HS and mixtures thereof. Zeolite A has the formula $Na_{12}[AlO_2)_{12}(SiO_2)_{12}].xH_2O$ wherein x is from 20 to 30, especially 27. Zeolite X has the formula $Na_{86}[(AlO_2)_{86}(SiO_2)_{106}]$. $276H_2O$.

Typically when the amine reaction product is mixed with a carrier and further processed to form a coated particle, the amine reaction product will be present in an amount of from 1 to 75%, preferably 5 to 30%, more preferably 6 to 25% by weight of the processed reaction product in the produced particle.

Typically the coating agent will be present in an amount of from 10% to 95%, preferably from 30 to 90%, more preferably, 50 to 75% by weight of the particle of the processed amine reaction product. In this instance, the amount of carrier will be sufficient to add up to 100%. Of course, the coated particle may also contain minors but in quantities which will not exceed either of the amount of carrier material or coating agent.

Preferred coating materials are selected from carbonate, starch, cyclodextrin, zeolites, and mixtures thereof.

The surface treatment of the particle can be carried out in a number of ways using equipment known in the art and the process may take in batch wise or continuous fashion.

One method for applying the coating material involves agglomeration. Any conventional agglomerator/mixer may be used including, but not limited to pan, rotary drum and vertical blender types as well as CB or KM mixing apparatus. Molten coating compositions may also be applied either by being poured onto, or spray atomized onto a moving bed of the mixture of amine reaction product with carrier.

Another method for applying the coating is to pour the obtained mixture (so-called particle), as herein before described, onto the coating material and agglomerate it in a Braun Mixer. Care is also taken that the temperature during the mixing and/or coating step does not substantially exceed the melting point of the carrier material. For example, 150 g of a mixture containing TAE80 and 20% of the amine reaction product is poured at 60° C. into a Braun Mixer containing 300 g of carbonate. The mixing of the ingredients is carried out for about 5 minutes. Care is also taken that the temperature during the coating does not exceed 65° C. The agglomerated particle can then be used as is for incorporation into the finished composition.

Accordingly, there is provided a processed amine reaction product as obtainable by the process of the invention.

If desired, the coated particle may also contain one or more additional ingredients like a surfactant for improved solubility or dispersability. Typical of such surfactant are the anionic, nonionic, or cationic surfactants. Preferably, the weight ratio of such additional ingredient(s) to the coating agent is of up to 1:1.

In another preferred marketing execution, an additional coating on the coated particle can be provided, which depending on the nature of this additional coating will give improved storage stability, flowability and/or improved fabric substantivity of the coated particle. One typical example is polyvinyl alcohol.

Incorporation into Finished Composition

The finished compositions aspect of the invention, including laundry compositions, hard surface cleaning compositions, personal cleaning compositions, spray-on products like odor-absorbing composition, dewrinkling composition, comprises the incorporation of the hereinbefore described processed amine reaction product or particle when processed with a carrier and optional coating together with one or more ingredient of the finished composition. Finished compositions incorporating the processed amine reaction product will normally contain from 0.01 to 25%, more preferably from 0.02 to 10%, and most preferably from 0.05 to 5% of the processed product on a composition weight basis.

Laundry compositions also encompass compositions providing color care, as well as compositions suitable for use in any steps of the domestic treatment, that is as a pre-treatment composition, as a wash additive as a composition suitable for use in the rinse-cycle of the laundry cycle or applied on a dryer-sheet. Obviously, multiple applications can be made such as treating the fabric with a pre-treatment composition of the invention and also thereafter with a composition of the invention suitable for use in the rinse cycle and/or suitable for use as a dryer-sheet.

The liquid finished compositions of the invention may also be in a spray, foam, or aerosol form which for example can be suitable for use while ironing, or applied on the surfaces of the tumble dryer.

As mentioned hereinbefore, the incorporation of the processed amine reaction product is conveniently made depending on its end form by dry-addition, as is or in coated form.

Laundry compositions encompass laundry detergent compositions, including liquid, solid form like powdered, tablets as well as softening compositions including rinse added softening composition as well as dryer added softening compositions.

A conventional disclosure of softening ingredients to be used in the softening composition of the invention can be found in EP 98870227.0, incorporated herein by reference.

Preferably, the finished composition is a detergent composition, more preferably in solid form.

In particular, it is preferred that the detergent composition comprises a clay.

Clay

The compositions of the invention may preferably contain a clay, preferably present at a level of from 0.05% to 40%, more preferably from 0.5% to 30%, most preferably from 2% to 20% by weight of the composition. For clarity, it is noted that the term clay mineral compound, as used herein, excludes sodium aluminosilicate zeolite builder compounds, which however, may be included in the compositions of the invention as optional components.

One preferred clay may be a bentonite clay. Highly preferred are smectite clays, as for example disclosed in the U.S. Pat. Nos. 3,862,058 3,948,790, 3,954,632 and 4,062, 647 and European Patents No.s EP-A-299,575 and EP-A-313,146 all in the name of the Procter and Gamble Company.

The term smectite clays herein includes both the clays in which aluminium oxide is present in a silicate lattice and the clays in which magnesium oxide is present in a silicate lattice. Smectite clays tend to adopt an expandable three layer structure.

Specific examples of suitable smectite clays include those selected from the classes of the montmorillonites, hectorites, volchonskoites, nontronites, saponites and sauconites, particularly those having an alkali or alkaline earth metal ion within the crystal lattice structure. Sodium or calcium montmorillonite are particularly preferred.

Suitable smectite clays, particularly montmorillonites, are sold by various suppliers including English China Clays, Laviosa, Georgia Kaolin and Colin Stewart Minerals.

Clays for use herein preferably have a particle dimension of from 10 nm to 800 nm more preferably from 20 nm to 500 mm, most preferably from 50 nm to 200 mm.

Particles of the clay mineral compound may be included as components of agglomerate particles containing other detergent compounds. Where present as such components, the term "largest particle dimension" of the clay mineral compound refers to the largest dimension of the clay mineral component as such, and not to the agglomerated particle as a whole.

Substitution of small cations, such as protons, sodium ions, potassium ions, magnesium ions and calcium ions, and of certain organic molecules including those having positively charged functional groups can typically take place within the crystal lattice structure of the smectite clays. A clay may be chosen for its ability to preferentially absorb one cation type, such ability being assessed by measurements of relative ion exchange capacity. The smectite clays suitable herein typically have a cation exchange capacity of at least 50 meq/100 g. U.S. Pat. No. 3,954,632 describes a method for measurement of cation exchange capacity.

The crystal lattice structure of the clay mineral compounds may have, in a preferred execution, a cationic fabric softening agent substituted therein. Such substituted clays have been termed 'hydrophobically activated' clays. The cationic fabric softening agents are typically present at a weight ratio, cationic fabric softening agent to clay, of from 1:200 to 1:10, preferably from 1:100 to 1:20. Suitable cationic fabric softening agents include the water insoluble tertiary amines or dilong chain amide materials as disclosed in GB-A-1 514 276 and EP-B-0 011 340.

A preferred commercially available "hydrophobically activated" clay is a bentonite clay containing approximately 40% by weight of a dimethyl ditallow quaternary ammonium salt sold under the tradename Claytone EM by English China Clays International.

In a highly preferred embodiment of the invention, the clay is present in an intimate mixture or in a particle with a humectant and a hydrophobic compound, preferably a wax or oil, such as paraffin oil. Preferred humectants are organic compounds, including propylene glycol, ethylene glycol, dimers or trimers of glycol, most preferably glycerol. The particle is preferably an agglomerate. Alternatively, the particle may be such that the wax or oil and optionally the humectant form an encapsulate on the clay or alternatively, the clay be a encapsulate for the wax or oil and the humectant. It may be preferred that the particle comprises an organic salt or silica or silicate.

However, in another embodiment of the invention, the clay is preferably mixed with one or more surfactants and optionally builders and optionally water, in which case the mixture is preferably subsequently dried. Preferably, such a mixture is further processed in a spray-drying method to obtain a spray dried particle comprising the clay.

It may be preferred that the flocculating agent is also comprised in the particle or granule comprising the clay.

It may also be preferred that the intimate mixture comprises a chelating agent.

Flocculating Agent

The compositions of the invention may contain a clay flocculating agent, preferably present at a level of from 0.005% to 10%, more preferably from 0.05% to 5%, most preferably from 0.1% to 2% by weight of the composition.

The clay flocculating agent functions such as to bring together the particles of clay compound in the wash solution and hence to aid their deposition onto the surface of the fabrics in the wash. This functional requirement is hence different from that of clay dispersant compounds which are commonly added to laundry detergent compositions to aid the removal of clay soils from fabrics and enable their dispersion within the wash solution.

Preferred as clay flocculating agents herein are organic polymeric materials having an average weight of from 100,000 to 10,000,000, preferably from 150,000 to 5,000,000, more preferably from 200,000 to 2,000,000.

Suitable organic polymeric materials comprise homopolymers or copolymers containing monomeric units selected from alkylene oxide, particularly ethylene oxide, acrylamide, acrylic acid, vinyl alcohol, vinyl pyrrolidone, and ethylene imine. Homopolymers of, on particular, ethylene oxide, but also acrylamide and acrylic acid are preferred.

European Patents No.s EP-A-299,575 and EP-A-313,146 in the name of the Procter and Gamble Company describe preferred organic polymeric clay flocculating agents for use herein.

The weight ratio of clay to the flocculating polymer is preferably from 1000:1 to 1:1, more preferably from 500:1 to 1:1, most preferably from 300:1 to 1:1, or even more preferably from 80:1 to 10:1, or in certain applications even from 60:1 to 20:1.

Inorganic clay flocculating agents are also suitable herein, typical examples of which include lime and alum.

The flocculating agent is preferably present in a detergent base granule such as a detergent agglomerate, extrudate or spray-dried particle, comprising generally one or more surfactants and builders.

Effervescent

Effervescent means may also be optionally used in the compositions of the invention.

Effervescency as defined herein means the evolution of bubbles of gas from a liquid, as the result of a chemical reaction between a soluble acid source and an alkali metal carbonate, to produce carbon dioxide gas, i.e. $C_6H_8O_7 + 3NaHCO_3 \rightarrow Na_3C_6H_5O_7 + 3CO_2\uparrow + 3H_2O$ Further examples of acid and carbonate sources and other effervescent systems may be found in: (Pharmaceutical Dosage Forms: Tablets Volume 1 Page 287 to 291).

Carbonate Salts

Suitable alkali and/or earth alkali inorganic carbonate salts herein include carbonate and hydrogen carbonate of potassium, lithium, sodium, and the like amongst which sodium and potassium carbonate are preferred. Suitable bicarbonates to be used herein include any alkali metal salt of bicarbonate like lithium, sodium, potassium and the like, amongst which sodium and potassium bicarbonate are preferred. However, the choice of carbonate or bicarbonate or mixtures thereof may be made depending on the pH desired in the aqueous medium wherein the granules are dissolved. For example where a relative high pH is desired in the aqueous medium (e.g., above pH 9.5) it may be preferred to use carbonate alone or to use a combination of carbonate and bicarbonate wherein the level of carbonate is higher than the level of bicarbonate. The inorganic alkali and/or earth alkali carbonate salt of the compositions of the invention comprises preferably a potassium or more preferably a sodium salt of carbonate and/or bicarbonate. Preferably, the carbonate salt comprises sodium carbonate, optionally also a sodium bicarbonate.

The inorganic carbonate salts herein are preferably present at a level of at least 20% by weight of the composition. Preferably they are present at a level of at least 23% or even 25% or even 30% by weight, preferably up to about 60% by weight or more preferably up to 55% or even 50% by weight.

They may be added completely or partially as separate powdered or granular component, as co-granules with other detergent ingredients, for example other salts or surfactants. In solid detergent compositions of the invention, they may also completely or partially be present in detergent granules such as agglomerates or spray dried granules.

In one embodiment of the invention, an effervescence source is present, preferably comprising an organic acid, such as carboxylic acids or aminoacids, and a carbonate. Then it may be preferred that part or all of the carbonate salt herein is premixed with the organic acid, and thus present in an separate granular component.

Preferred effervescent source are selected from compressed particles of citric acid and carbonate optionally with a binder; and particle of carbonate, bicarbonate and malic or maleic acid in weight ratios of 4:2:4. The dry add form of citric acid and carbonate are preferably used.

The carbonate may have any particle size. In one embodiment, in particular when the carbonate salt is present in a granule and not as separately added compound, the carbonate salt has preferably a volume median particle size from 5 to 375 microns, whereby preferably at least 60%, preferably at least 70% or even at least 80% or even at least 90% by volume, has a particle size of from 1 to 425 microns. More preferably, the carbon dioxide source has a volume median particle size of 10 to 250, whereby preferably at least 60%, or even at least 70% or even at least 80% or even at least 90% by volume, has a particle size of from 1 to 375 microns; or even preferably a volume median particle size from 10 to 200 microns, whereby preferably at least 60%, preferably at least 70% or even at least 80% or even at least 90% by volume, has a particle size of from 1 to 250 microns.

In particular when the carbonate salt is added as separate component, so to say 'dry-added' or admixed to the other detergent ingredients, the carbonate may have any particle size, including the above specified particle sizes, but preferably at least an volume average particle size of 200 microns or even 250 microns or even 300 microns.

It may be preferred that the carbon dioxide source of the required particle size is obtained by grinding a larger particle size material, optionally followed by selecting the material with the required particle size by any suitable method.

Whilst percarbonate salts may be present in the compositions of the invention as a bleaching agent, they are not included in the carbonate salts as defined herein.

The preferred detergent composition, embodiment of the invention, will, preferably contain a bleach precursor, a source of alkaline hydrogen peroxide necessary to form a peroxyacid bleaching species in the wash solution and preferably will also contain other components conventional in detergent compositions. Thus, preferred detergent compositions will incorporate one or more of surfactants, organic and inorganic builders, soil suspending and anti-redeposition agents, suds suppressors, enzymes, fluorescent whitening agents, photoactivated bleaches, perfumes, colours, and mixtures thereof.

Typical disclosure of such components can be found in EP-A-0,659,876 and European patent application No. 98870226.2 which are both incorporated herein by reference.

Form of the Composition

The composition of the invention may take a variety of physical form including liquid, gel, foam in either aqueous or non-aqueous form, granular and tablet forms.

Still in another aspect of the invention, there is provided a packaged composition comprising the processed product of the invention or composition of the invention. Preferably, the packaged composition is a closed packaging system having a moisture vapour transmission rate of less than 20 g/m²/24 hours. Typical disclosure of such a package can be found in WO 98/40464.

Still another preferred package is a spray dispenser.

Spray Dispenser

The present invention also relates to such compositions incorporated into a spray dispenser to create an article of manufacture that can facilitate treatment of fabric articles and/or surfaces with said compositions containing the amine reaction product and other ingredients (examples are cyclo-dextrins, polysaccharides, polymers, surfactant, perfume, softener) at a level that is effective, yet is not discernible when dried on the surfaces. The spray dispenser comprises manually activated and non-manual powered (operated) spray means and a container containing the treating composition. Typical disclosure of such spray dispenser can be found in WO 96/04940 page 19 line 21 to page 22 line 27. The articles of manufacture preferably are in association with instructions for use to ensure that the consumer applies sufficient ingredient of the composition to provide the desired benefit. Typical compositions to be dispensed from a sprayer contain a level of amine reaction product of from about 0.01% to about 5%, preferably from about 0.05% to about 2%, more preferably from about 0.1% to about 1%, by weight of the usage composition.

Method of Use

Also provided herein is a method for providing a delayed release of an active ketone or aldehyde which comprises the step of contacting the surface to be treated with a a compound or composition of the invention, and thereafter contacting the treated surface with a material, preferably an aqueous medium like moisture or any other means susceptible of releasing the active from the amine reaction product.

By "surface", it is meant any surface onto which the compound can deposit. Typical examples of such material are fabrics, hard surfaces such as dishware, floors, bathrooms, toilet, kitchen, skin, paper, and other surfaces in need of a delayed release of a perfume ketone and/or aldehyde such as that with litter like animal litter. Preferably, the surface is selected from a fabric, a tile, a ceramic; more preferably is a fabric.

By "delayed release" is meant release of the active component (e.g perfume) over a longer period of time than by the use of the active (e.g., perfume) itself.

Still in another aspect of the invention, there is provided the use of the product of the invention for the manufacture of a laundry and cleaning composition for delivering residual fragrance and fabric care, in particular color care, onto the fabrics on which it is applied.

The following are synthesis examples of compounds as defined in the present invention:

I—Synthesis of ethyl 4-aminobenzoate with 2,4-dimethyl-3-cyclohexen-1-carboxaldehyde In a reaction vessel of 6 l, 1248 g of ethyl 4-aminobenzoate and 1040 g of 2,4-dimethyl-3-cyclohexen-1-carboxaldehyde in a weight ratio of amine compound to perfume of 1:1.2 are mixed together and placed on a rotary evaporator, with a water bath of 42° C. The temperature of the reaction mixture, during the mixing, is controlled and not allowed to go higher than 50° C. The reaction mixture is stirred at 20–100 rpm at 50° C. for 4 hours. After these 4 hours, all of the ethyl-4-aminobenzoate is completely dissolved. The use of a temperature of reaction of 50° C. is chosen as it enables a better dissolution of the ethyl-4-aminobenzoate. Once all the ethyl-4-aminobenzoate is dissolved, the reaction mixture is mixed for a further 4 hours at 50 C under vacuum created with a pump, i.e. a "Leybold Triviac" which is protected by a carbonic ice trap. 2182 g of amine reaction product is obtained. The level of the unreacted 2,4-dimethyl-3-cyclohexen-1-carboxaldehyde is lower than 5% and only traces of water remaining.

II—Synthesis of 1,4-bis-(3-aminopropyl)-piperazine with δ-Damascone

In a reaction vessel of 2 l, placed on a rotary evaporator, 800 of δ-Damascone and 424 g of 1,4-bis-(3-aminopropyl)-piperazine are mixed together for 4 hours at 42° C. The temperature of the reaction mixture, during the mixing, which is stirred at 20–100 rpm, is controlled by means of a water bath and not allowed to go higher than 42° C.; the temperature inside the reaction container is of 40° C. Subsequently, the reaction mixture is mixed for ½ hour at 42° C. under vacuum. 1224 g of amine reaction product is obtained. Only traces of unreacted 1,4-bis-(3-aminopropyl)-piperazine and δ -Damascone remain.

III—Synthesis of Lupasol with α- or δ-Damascone or 2,4-dimethyl-3-cyclohexen-1-carboxaldehyde A. In a reaction vessel of 2 l, placed on a rotary evaporator, 1500 g of δ-Damascone and 1800 g of Lupasol HF(about 50% of water) are mixed together for 4 hours at 42° C. at a stirring rate of 20 to 100 rpm. The temperature of the reaction mixture, during the mixing, is controlled by means of a water bath and not allowed to go higher than 42° C.; the temperature inside the reaction container is of 40° C. Subsequently, the reaction mixture is kept during 16 hours at 42° C. under vacuum to remove most of the water from the reaction vessel. 2741 g of product is obtained and only traces of unreacted δ-Damascone remain.

B. In a reaction vessel of 6 l, placed on a rotary evaporator, 614 g of 2,4-dimethyl-3-cyclohexen-1-carboxaldehyde and 1110 g of LupasolG100 (about 50% of water) are mixed together for 4 hours at 42 C. under vacuum (1 mm/Hg). The temperature of the reaction mixture, during the mixing which is stirred at 20–100 rpm, is controlled by means of a water bath and not allowed to go higher than 42 C.; the temperature inside the reaction container is of 40° C.

Subsequently, the reaction mixture is kept during 16 hours at 42 C. under vacuum to remove most of the water from the reaction vessel. 1363 g of amine reaction product is obtained and only traces of unreacted 2,4-dimethyl-3-cyclohexen-1-carboxaldehyde remain.

C. In a reaction vessel of 4l, placed on a rotary evaporator, 800 g of α-Damascone and 960 g of LupasolG35 (about 50% of water) are mixed together at 25C for 17 hours under vacuum (1 mm/Hg). The temperature of the reaction mixture, during the mixing, is controlled and not allowed to go higher than 30C. Subsequently, the reaction mixture is kept during 2hours at 42C under vacuum to remove most of the water form the reaction vessel. 1275 g of amine reaction product is obtained and only traces (i.e. less than 1% by weight) of unreacted α-Damascone and water remain.

The obtained amine reaction product may be used as is by spraying or further processed to enable easy incorporation into finished product.

Various processing method may be used like mixing with a carrier and optionally coating the obtained particle. When the carrier has a boiling point between 5 and 200° C., it may be desirable to remove the carrier from the finished particle.

Still another processing method is by mixing with a liquid carrier like an hydrophobic perfume composition, thereby enabling direct spraying. Typical perfume composition is as follows:

| | |
|---|---|
| Citronellol | 7 |
| Geraniol | 7 |
| Linalool | 7 |
| Para Tertiary Butyl Cyclohexyl Acetate | 10 |
| Phenyl Ethyl Alcohol | 19 |
| Habanolide | 4.5 |
| Para Methoxy Acetophenone | 1.5 |
| Benzyl Acetate | 4 |
| Eugenol | 2 |
| Phenyl Ethyl Acetate | 5 |
| Verdyl Acetate | 6 |
| Verdyl Propionate | 4 |
| Hexyl Cinnamic Aldehyde | 3 |
| Ionone Gamma Methyl | 2 |
| Methyl Cedrylone | 10 |
| P.T. Bucinal | 7 |
| Para Cresyl Methyl Ether | 1 |

Processing Method

Processing of the amine reaction product with the carrier is done as hereinbefore described. In particular, 20 g of amine reaction product as above synthesised is mixed in an Ultra Turrax containing 80 g of carrier, e.g. TAE80 for 5 minutes, the temperature of mixing being of about 70° C., and the speed of the mixer being sufficient so as to maintain such temperature substantially constant. Temperature and time will depend on the nature of the carrier but are conventional steps to the skilled man. The resulting mixture is maintained at a temperature substantially equal to the melting point of the carrier material. Once the mixture is at a suitable temperature, it is poured onto the coating material and agglomerated in an electrical mixer like a Braun Mixer. Care is also taken that the temperature during the mixing does not substantially exceed the melting point of the carrier material. For example, 150 g of a mixture containing TAE80 and 20% of the amine reaction product is poured at 60° C. into a Braun Mixer containing 300 g of carbonate. The mixing of the ingredients is carried out for about 5 minutes. Care is also taken that the temperature during the mixing does not exceed 65° C. Again, temperature and time will depend on the nature of the coating agent but are conventional steps to the skilled man.

Still another processing method is the processing of the amine reaction product with an acid carrier as hereinbefore described. In particular, 10 g of the δ-Damascone-Lupasol HF, as synthesized above, was dissolved in 70 ml of dry ethanol. Separately, 5 g of anhydrous citric acid was dissolved in 80 ml of dry ethanol. The solution were added slowly together in glass container while mixing, by addition of the Lupasol HF-δ-Damascone solution to the citric acid solution. The temperature during the mixing is kept at room temperature. After the addition is complete, 1 g anhydrous citric acid is added till a complete precipitation of the Lupasol HF-δ-Damascone is obtained. The precipitation is filtered off and dried. About 16 g of the salt is obtained. Total time for the experiment is about 1 hour.

Processing Method for the Coating

If a coating is desired, the obtained mixture (so-called particle), as herein before described, is pour onto the coating material and agglomerated it in a Braun Mixer. Care is taken that the temperature during the mixing and/or coating step does not substantially exceed the melting point of the carrier material. For example, 130 g of a mixture containing the citric acid salt of the amine reaction product and 39 g of PEG 4000 is poured at 60° C. into a Braun Mixer containing 50 g of carbonate. The mixing of the ingredients is carried out for about 5 minutes. Care is also taken that the temperature during the coating does not exceed 60° C.

Abbreviations Used in the following Laundry and Cleaning Composition Examples

In the laundry and cleaning compositions, the abbreviated component identifications have the following meanings:

| | |
|---|---|
| DEQA | Di-(tallowyl-oxy-ethyl) dimethyl ammonium chloride |
| DTDMAC | Ditallow dimethylammonium chloride |
| DEQA (2) | Di-(soft-tallowyloxyethyl) hydroxyethyl methyl ammonium methylsulfate. |
| DTDMAMS | Ditallow dimethyl ammonium methylsulfate. |
| SDASA | 1:2 ratio of stearyldimethyl amine:triple-pressed stearic acid. |
| Fatty acid | Stearic acid of IV = 0 |
| Electrolyte | Calcium chloride |
| PEG | Polyethylene Glycol 4000 |
| Neodol 45-13 | C14–C15 linear primary alcohol ethoxylate, sold by Shell Chemical CO. |
| Silicone antifoam | Polydimethylsiloxane foam controller with siloxane-oxyalkylene copolymer as dispersing agent with a ratio of said foam controller to said dispersing agent of 10:1 to 100:1. |
| PEI | Polyethyleneimine with an average molecular weight of 1800 and an average ethoxylation degree of 7 ethyleneoxy residues per nitrogen |
| HEDP | 1,1-hydroxyethane diphosphonic acid |
| LAS | Sodium linear $C_{11-13}$ alkyl benzene sulfonate |
| TAS | Sodium tallow alkyl sulfate |
| CxyAS | Sodium $C_{1x}$–$C_{1y}$ alkyl sulfate |
| C46SAS | Sodium $C_{14}$–$C_{16}$ secondary (2,3) alkyl sulfate |
| CxyEzS | Sodium $C_{1x}$–$C_{1y}$ alkyl sulfate condensed with z moles of ethylene oxide |
| CxyEz | $C_{1x}$–$C_{1y}$ predominantly linear primary alcohol condensed with an average of z moles of ethylene oxide |
| QAS | $R_2.N^+(CH_3)_2(C_2H_4OH)$ with $R_2 = C_{12}$–$C_{14}$ |
| QAS 1 | $R_2.N^+(CH_3)_2(C_2H_4OH)$ with $R_2 = C_8$–$C_{11}$ |
| APA | $C_8$–$C_{10}$ amido propyl dimethyl amine |
| Soap | Sodium linear alkyl carboxylate derived from an 80/20 mixture of tallow and coconut fatty acids |
| STS | Sodium toluene sulphonate |
| CFAA | $C_{12}$–$C_{14}$ (coco) alkyl N-methyl glucamide |
| TFAA | $C_{16}$–$C_{18}$ alkyl N-methyl glucamide |

-continued

| | |
|---|---|
| TPKFA | $C_{12}$–$C_{14}$ topped whole cut fatty acids |
| STPP | Anhydrous sodium tripolyphosphate |
| TSPP | Tetrasodium pyrophosphate |
| Zeolite A | Hydrated sodium aluminosilicate of formula $Na_{12}(AlO_2SiO_2)_{12}.27H_2O$ having a primary particle size in the range from 0.1 to 10 micrometers (weight expressed on an anhydrous basis) |
| NaSKS-6 | Crystalline layered silicate of formula δ- $Na_2Si_2O_5$ |
| Citric acid | Anhydrous citric acid |
| Borate | Sodium borate |
| Carbonate | Anydrous sodium carbonate with a particle size between 200 μm and 900 μm |
| Bicarbonate | Anhydrous sodium bicarbonate with a particle size distribution between 400 μm and 1200 μm |
| Silicate | Amorphous sodium silicate ($SiO_2:Na_2O$ = 2.0:1) |
| Sulfate | Anhydrous sodium sulfate |
| Mg sulfate | Anhydrous magnesium sulfate |
| Citrate | Tri-sodium citrate dihydrate of activity 86.4% with a particle size distribution between 425 μm and 850 μm |
| MA/AA | Copolymer of 1:4 maleic/acrylic acid, average molecular weight about 70,000 |
| MA/AA (1) | Copolymer of 4:6 maleic/acrylic acid, average molecular weight about 10,000 |
| AA | Sodium polyacrylate polymer of average molecular weight 4,500 |
| CMC | Sodium carboxymethyl cellulose |
| Cellulose ether | Methyl cellulose ether with a degree of polymerization of 650 available from Shin Etsu Chemicals |
| Protease | Proteolytic enzyme, having 3.3% by weight of active enzyme, sold by NOVO Industries A/S under the tradename Savinase |
| Protease I | Proteolytic enzyme, having 4% by weight of active enzyme, as described in WO 95/10591, sold by Genencor Int. Inc. |
| Alcalase | Proteolytic enzyme, having 5.3% by weight of active enzyme, sold by NOVO Industries A/S |
| Cellulase | Cellulytic enzyme, having 0.23% by weight of active enzyme, sold by NOVO Industries A/S under the tradename Carezyme |
| Amylase | Amylolytic enzyme, having 1.6% by weight of active enzyme, sold by NOVO Industries A/S under the tradename Termamyl 120T |
| Lipase | Lipolytic enzyme, having 2.0% by weight of active enzyme, sold by NOVO Industries A/S under the tradename Lipolase |
| Lipase (1) | Lipolytic enzyme, having 2.0% by weight of active enzyme, sold by NOVO Industries A/S under the tradename Lipolase Ultra |
| Endolase | Endoglucanase enzyme, having 1.5% by weight of active enzyme, sold by NOVO Industries A/S |
| PB4 | Sodium perborate tetrahydrate of nominal formula $NaBO_2.3H_2O.H_2O_2$ |
| PB1 | Anhydrous sodium perborate bleach of nominal formula $NaBO_2.H_2O_2$ |
| Percarbonate | Sodium percarbonate of nominal formula $2Na_2CO_3.3H_2O_2$ |
| NOBS | Nonanoyloxybenzene sulfonate in the form of the sodium salt |
| NAC-OBS | (6-nonamidocaproyl) oxybenzene sulfonate |
| TAED | Tetraacetylethylenediamine |
| DTPA | Diethylene triamine pentaacetic acid |
| DTPMP | Diethylene triamine penta (methylene phosphonate), marketed by Monsanto under the Tradename Dequest 2060 |
| EDDS | Ethylenediamine-N,N'-disuccinic acid, (S,S) isomer in the form of its sodium salt. |
| Photoactivated bleach (1) | Sulfonated zinc phthlocyanine encapsulated in dextrin soluble polymer |
| Photoactivated bleach (2) | Sulfonated alumino phthlocyanine encapsulated in dextrin soluble polymer |
| Brightener 1 | Disodium 4,4'-bis(2-sulphostyryl)biphenyl |
| Brightener 2 | Disodium 4,4'-bis(4-anilino-6-morpholino-1.3.5-triazin-2-yl)amino) stilbene-2,2'-disulfonate |
| HEDP | 1,1-hydroxyethane diphosphonic acid |
| PEGx | Polyethylene glycol, with a molecular weight of x (typically 4,000) |
| PEO | Polyethylene oxide, with an average molecular weight of 200000 to 400000 |
| TEPAE | Tetraethylenepentaamine ethoxylate |
| PVI | Polyvinyl imidosole, with an average molecular weight of 20,000 |
| PVP | Polyvinylpyrolidone polymer, with an average molecular weight of 60,000 |
| PVNO | Polyvinylpyridine N-oxide polymer, with an average molecular weight of 50,000 |
| PVPVI | Copolymer of polyvinylpyrolidone and vinylimidazole, with an average molecular weight of 20,000 |
| QEA | $bis((C_2H_5O)(C_2H_4O)_n)(CH_3)$ —$N^+$—$C_6H_{12}$—$N^+$— $(CH_3)bis((C_2H_5O)$—$(C_2H_4O))_n$, wherein n = from 20 to 30 |
| SRP 1 | Anionically end capped poly esters |
| SRP 2 | Diethoxylated poly (1,2 propylene terephtalate) short block polymer |
| PEI | Polyethyleneimine with an average molecular weight of 1800 and an average ethoxylation degree of 7 ethyleneoxy residues per nitrogen |
| Silicone antifoam | Polydimethylsiloxane foam controller with siloxane-oxyalkylene copolymer as dispersing agent with a ratio of said foam controller to said dispersing agent of 10:1 to 100:1 |
| Opacifier | Water based monostyrene latex mixture, sold by BASF Aktiengesellschaft under the tradename Lytron 621 |
| Wax | Paraffin wax |
| PA30 | Polyacrylic acid of average molecular weight of between about 4,500–8,000. |
| 480N | Random copolymer of 7:3 acrylate/methacrylate, average molecular weight about 3,500. |
| Polygel/carbopol | High molecular weight crosslinked polyacrylates. |
| Metasilicate | Sodium metasilicate ($SiO_2:Na_2O$ ratio = 1.0). |
| Nonionic | $C_{13}$–$C_{15}$ mixed ethoxylated/propoxylated fatty alcohol with an average degree of ethoxylation of 3.8 and an average degree of propoxylation of 4.5. |
| Neodol 45-13 | C14–C15 linear primary alcohol ethoxylate, sold by Shell Chemical CO. |
| MnTACN | Manganese 1,4,7-trimethyl-1,4,7-triazacyclononane. |
| PAAC | Pentaamine acetate cobalt(III) salt. |
| Paraffin | Paraffin oil sold under the tradename Winog 70 by Wintershall. |
| NaBz | Sodium benzoate. |
| BzP | Benzoyl Peroxide. |
| SCS | Sodium cumene sulphonate. |
| BTA | Benzotriazole. |
| PH | Measured as a 1% solution in distilled water at 20° C. |
| PARP1 | Processed amine reaction product of ethyl 4-aminobenzoate with 2,4-dimethyl-3-cyclohexen-1-carboxaldehyde as made from Synthesis example I, mixed with a carrier and agglomerated with TAE80 coating agent according to processing method above described. |
| PARP2 | Processed amine reaction product of Lupasol G35 with α-Damascone as made from Synthesis example III, mixed with citric acid carrier and agglomerated with PEG4000 and carbonate coating agent according to processing method above described. |
| PARP3 | Processed amine reaction product of Lupasol HF with δ-Damascone as made from Synthesis example III, mixed with a carrier and agglomerated with TAE80 coating agent according to processing method above described. |
| PARP4 | Processed amine reaction product of BNPP with δ-Damascone as made from Synthesis example II, mixed with a carrier and agglomerated with PEG4000 coating agent according to processing method above described. |
| PARP5 | Processed amine reaction product of LupasolG100 with 2,4-dimethyl-3-cyclohexen-1-carboxaldehyde. as made from Synthesis example III, mixed with a carrier and agglomerated with TAE80 coating agent according to processing method above described. |
| PARP6 | Processed amine reaction product of ethyl 4-aminobenzoate with trans-2-nonenal as made from Synthesis example I, mixed with a carrier and agglomerated with TAE80 coating agent according to processing method above described. |

| | | |
|---|---|---|
| PARP7 | Processed amine reaction product of Lupasol HF with δ-Damascone as made from Synthesis example III, mixed with citric acid carrier according to processing method above described. | |
| Clay I | Bentonite clay | |
| Clay II | Smectite clay | |
| Flocculating agent I | polyethylene oxide of average molecular weight of between 200,000 and 400,000 | |
| Flocculating agent II | polyethylene oxide of average molecular weight of between 400,000 and 1,000,000 | |
| Flocculating agent III | polymer of acrylamide and/or acrylic acid of average molecular weight of 200,000 and 400,000 | |
| DOBS | Decanoyl oxybenzene sulfonate in the form of the sodium salt | |
| SRP 3 | Polysaccharide soil release polymer | |
| SRP 4 | Nonionically end capped poly esters | |
| Polymer | Polyvinylpyrrolidone K90 available from BASF under the tradename Luviskol K90 | |
| Dye fixative | Dye fixative commercially available from Clariant under the tradename Cartafix CB | |
| Polyamine | 1,4-Bis-(3-aminopropyl)piperazine | |
| Bayhibit AM | 2-Phosphonobutane-1,2,4-tricarboxylic acid commercially available from Bayer | |
| Fabric softener active | Di-(canoloyl-oxy-ethyl)hydroxyethyl methyl ammonium methylsulfate | |
| HPBDC | Hydroxypropyl beta-cyclodextrin | |
| RAMEB | Randomly methylated beta-cyclodextrin | |
| Bardac 2050 | Dioctyl dimethyl ammonium chloride, 50% solution | |
| Bardac 22250 | Didecyl dimethyl ammonium chloride, 50% solution | |
| Genamin C100 | Coco fatty amine ethoxylated with 10 moles ethylene oxide and commercially available from Clariant | |
| Genapol V4463 | Coco alcohol ethoxylated with 10 moles ethylene oxide and commercially available from Clariant | |
| Silwet 7604 | Polyalkyleneoxide polysiloxanes of MW 4000 of formula R-(CH$_3$)$_2$SiO—[(CH$_3$)$_2$SiO]$_a$—[(CH$_3$)(R)SiO]$_b$—Si(CH$_3$)$_2$-R, wherein average a + b is 21, commercially available from Osi Specialties, Inc., Danbury, Connecticut | |
| Silwet 7600 | Polyalkyleneoxide polysiloxanes of MW 4000, of formula R-(CH$_3$)$_2$SiO—[(CH$_3$)$_2$SiO]$_a$—[(CH$_3$)(R)SiO]$_b$—Si(CH$_3$)$_2$-R, wherein average a + b is 11, and commercially available from Osi Specialties, Inc., Danbury, Connecticut | |

In the following formulation examples all levels are quoted as % by weight of the composition unless otherwise stated, and incorporation of the processed amine reaction product so called herein after "PARP" in the fully formulated composition is carried out by dry addition in the composition as defined herein before. The term in bracket for the PARP in the formulation examples refers to the type of carrier (c) for carbonate carrier and (s) for starch carrier.

EXAMPLE 1

The following high density granular laundry detergent compositions are in accord with the invention:

| | A | B | C | D | E |
|---|---|---|---|---|---|
| LAS | 6.0 | 6.0 | 8.0 | 8.0 | 8.0 |
| TAS | 1.0 | 0.1 | — | 0.5 | — |
| C46(S)AS | — | — | 2.0 | 2.5 | — |
| C25AS | 4.5 | 5.5 | — | — | — |
| C68AS | — | — | 2.0 | 5.0 | 7.0 |
| C25E5 | 4.6 | 4.6 | — | — | 3.4 |
| C25E7 | — | — | 3.4 | 3.4 | 1.0 |
| C25E3S | 5.0 | 4.5 | — | — | — |
| QAS | — | — | — | 0.8 | — |
| QAS (I) | 0.5 | 1.0 | — | — | — |
| Zeolite A | 20.0 | 18.1 | 18.1 | 18.0 | 14.1 |
| Citric acid | — | 2.5 | — | — | — |
| Carbonate | 10.0 | 13.0 | 13.0 | 13.0 | 25.0 |
| SKS-6 | — | 10.0 | — | — | — |
| Silicate | 0.5 | 0.3 | 1.4 | 1.4 | 3.0 |
| Citrate | — | — | — | 1.0 | — |
| Sulfate | — | — | 26.1 | 26.1 | 26.1 |
| Mg sulfate | — | 0.2 | 0.3 | — | — |
| MA/AA | 1.0 | 1.0 | 0.3 | 0.3 | 0.3 |
| CMC | 0.4 | 0.4 | 0.2 | 0.2 | 0.2 |
| PB4 | — | — | 9.0 | 9.0 | 5.0 |
| Percarbonate | 18.0 | 18.0 | — | — | — |
| TAED | 3.9 | 4.2 | 1.5 | 0.4 | 1.5 |
| NAC-OBS | — | — | — | 2.0 | 1.0 |
| DTPMP | — | — | 0.25 | 0.25 | 0.25 |
| SRP 2 | — | 0.2 | — | — | — |
| EDDS | 0.5 | 0.5 | — | 0.25 | 0.4 |
| CFAA | — | — | — | 1.0 | — |
| HEDP | 0.4 | 0.4 | 0.3 | 0.3 | 0.3 |
| QEA | — | 0.5 | — | — | — |
| Protease I | — | — | — | — | 0.26 |
| Protease | 1.5 | 1.0 | 0.26 | 0.26 | — |
| Cellulase | 0.3 | 0.3 | 0.3 | — | — |
| Amylase | 0.5 | 0.5 | 0.1 | 0.1 | 0.1 |
| Lipase (1) | 0.5 | 0.5 | 0.3 | — | — |
| Photoactivated bleach (ppm) | 20 ppm | 20 ppm | 15 ppm | 15 ppm | 15 ppm |
| Brightener 1 | 0.09 | 0.09 | 0.09 | 0.09 | 0.09 |
| Perfume spray on | 0.4 | 0.4 | 0.3 | 0.3 | 0.3 |
| PARP 1 | — | — | 2.0(c) | 1.0(c) | — |
| PARP 2 | — | — | — | — | 0.8 |
| PARP 3 | 1.0(c) | 0.5(c) | — | — | — |
| PARP 4 | 2.0(c) | — | — | — | — |
| Silicone antifoam | 0.3 | 0.3 | 0.5 | 0.5 | 0.5 |
| Misc/minors to 100% | | | | | |
| Density in g/liter | 850 | 850 | 850 | 850 | 850 |

| | F | G | H | I |
|---|---|---|---|---|
| LAS | 2.0 | 6.0 | 6.0 | 5.0 |
| TAS | 0.5 | 1.0 | 0.1 | 1.5 |
| C25AS | 7.0 | 4.5 | 5.5 | 2.5 |
| C68AS | — | — | — | 0.2 |
| C25E5 | 10.0 | 4.6 | 4.6 | 2.6 |
| C25E3S | 2.0 | 5.0 | 4.5 | 0.5 |
| QAS (I) | 0.8 | 0.5 | 1.0 | 1.5 |
| Zeolite A | 18.1 | 20.0 | 18.1 | 16.2 |
| Citric acid | 2.5 | — | 2.5 | 1.5 |
| Carbonate | 10.0 | 10.0 | 13.0 | 20.6 |
| SKS-6 | 10.0 | — | 10.0 | 4.3 |
| Silicate | 0.3 | 0.5 | 0.3 | — |
| Citrate | 3.0 | — | — | 1.4 |
| Sulfate | 6.0 | — | — | — |
| Mg sulfate | 0.2 | — | 0.2 | 0.03 |
| MA/AA | 4.0 | 1.0 | 1.0 | 0.6 |
| CMC | 0.2 | 0.4 | 0.4 | 0.3 |
| Percarbonate | — | 18.0 | 18.0 | 9.0 |
| TAED | — | 3.9 | 4.2 | 3.2 |
| DTPMP | 0.25 | — | — | — |
| SRP 2 | 0.2 | — | 0.2 | — |
| EDDS | — | 0.5 | 0.5 | 0.1 |
| CFAA | 2.0 | — | — | — |
| TFAA | — | — | — | 1.1 |
| HEDP | 0.3 | 0.4 | 0.4 | 0.3 |
| QEA | 0.2 | — | 0.5 | — |
| Protease I | 1.0 | — | — | 0.3 |
| Protease | — | 1.5 | 1.0 | — |
| Cellulase | 0.3 | 0.3 | 0.3 | 0.3 |
| Amylase | 0.4 | 0.5 | 0.5 | 0.1 |
| Lipase (1) | 0.5 | 0.5 | 0.5 | 0.1 |
| Photoactivated bleach (ppm) | — | 20 ppm | 20 ppm | 20 ppm |
| PVNO/PVPVI | 0.1 | — | — | — |
| Brightener 1 | — | 0.09 | 0.09 | 0.01 |

-continued

|  | | | | |
|---|---|---|---|---|
| Brightener 2 | — | — | — | 0.09 |
| Perfume spray on | 0.4 | 0.4 | 0.4 | 0.4 |
| PARP 1 | — | 2.0(c) | 4.0(c) | — |
| PARP 2 | 2.0 | 1.0 | — | 0.8 |
| Silicone antifoam | — | 0.3 | 0.3 | 0.3 |
| Clay II | — | — | — | 12.0 |
| Flocculating agent I | — | — | — | 0.3 |
| Glycerol | — | — | — | 0.6 |
| Wax | — | — | — | 0.4 |
| Misc/minors to 100% | | | | |
| Density in g/liter | 850 | 850 | 850 | 850 |

EXAMPLE 2

The following granular laundry detergent compositions of particular utility under European machine wash conditions are in accord with the invention:

|  | A | B | C | D | E | F |
|---|---|---|---|---|---|---|
| LAS | 5.5 | 7.5 | 5.0 | 5.0 | 6.0 | 7.0 |
| TAS | 1.25 | 1.86 | — | 0.8 | 0.4 | 0.3 |
| C24AS/C25AS | — | 2.24 | 5.0 | 5.0 | 5.0 | 2.2 |
| C25E3S | — | 0.76 | 1.0 | 1.5 | 3.0 | 1.0 |
| C45E7 | 3.25 | — | — | — | — | 3.0 |
| TFAA | — | — | 2.0 | — | — | — |
| C25E5 | — | 5.5 | — | — | — | — |
| QAS | 0.8 | — | — | — | — | — |
| QAS II | — | 0.7 | 1.0 | 0.5 | 1.0 | 0.7 |
| STPP | 19.7 | — | — | — | — | — |
| Zeolite A | — | 19.5 | 25.0 | 19.5 | 20.0 | 17.0 |
| NaSKS-6/citric acid (79:21) | — | 10.6 | — | 10.6 | — | — |
| NaSKS-6 | — | — | 9.0 | — | 10.0 | 10.0 |
| Carbonate | 6.1 | 10.0 | 9.0 | 10.0 | 10.0 | 18.0 |
| Bicarbonate | — | 2.0 | 7.0 | 5.0 | — | 2.0 |
| Silicate | 6.8 | — | — | 0.3 | 0.5 | — |
| Citrate | — | — | 4.0 | 4.0 | — | — |
| Sulfate | 39.8 | — | — | — | 5.0 | 12.0 |
| Mg sulfate | — | — | 0.1 | 0.2 | 0.2 | — |
| MA/AA | 0.5 | 1.6 | 3.0 | 4.0 | 1.0 | 1.0 |
| CMC | 0.2 | 0.4 | 1.0 | 1.0 | 0.4 | 0.4 |
| PB4 | 5.0 | 12.7 | — | — | — | — |
| Percarbonate | — | — | — | — | 18.0 | 15.0 |
| TAED | 0.5 | 3.1 | — | — | 5.0 | — |
| NAC-OBS | 1.0 | 3.5 | — | — | — | 2.5 |
| DTPMP | 0.25 | 0.2 | — | 0.4 | — | 0.2 |
| HEDP | — | 0.3 | — | 0.3 | 0.3 | 0.3 |
| QEA | — | — | 1.0 | 1.0 | 1.0 | — |
| Protease I | — | — | — | 0.5 | 1.2 | — |
| Protease | 0.26 | 0.85 | 0.9 | 1.0 | — | 0.7 |
| Lipase (1) | 0.15 | 0.15 | 0.3 | 0.3 | 0.3 | 0.2 |
| Cellulase | 0.28 | 0.28 | 0.2 | 0.2 | 0.3 | 0.3 |
| Amylase | 0.1 | 0.1 | 0.4 | 0.4 | 0.6 | 0.2 |
| PVNO/PVPVI | — | — | 0.2 | 0.2 | — | — |
| PVP | 0.9 | 1.3 | — | — | — | 0.9 |
| SRP 1 | — | — | 0.2 | 0.2 | 0.2 | — |
| Photoactivated bleach (1) (ppm) | 15 ppm | 27 ppm | — | — | 20 ppm | 20 ppm |
| Photoactivated bleach (2) (ppm) | 15 ppm | — | — | — | — | — |
| Brightener 1 | 0.08 | 0.19 | — | — | 0.09 | 0.15 |
| Brightener 2 | — | 0.04 | — | — | — | — |
| Perfume | 0.3 | 0.3 | 0.4 | 0.3 | 0.4 | 0.3 |
| PARP1 | 2.0(c) | 1.0(c) | 4.0(c) | — | — | — |
| PARP3 | — | — | 1.0(c) | 2.0(s) | 1.5(c) | 0.4(c) |
| Silicone antifoam | 0.5 | 2.4 | 0.3 | 0.5 | 0.3 | 2.0 |
| Minors/misc to 100% | | | | | | |
| Density in g/liter | 750 | 750 | 750 | 750 | 750 | 750 |

EXAMPLE 3

The following detergent formulations of particular utility under European machine wash conditions were prepared in accord with the invention.

|  | A | B | C | D |
|---|---|---|---|---|
| Blown powder | | | | |
| LAS | 6.0 | 5.0 | 11.0 | 6.0 |
| TAS | 2.0 | — | — | 2.0 |
| Zeolite A | 24.0 | — | — | 20.0 |
| STPP | — | 27.0 | 24.0 | — |
| Sulfate | 4.0 | 6.0 | 13.0 | — |
| MA/AA | 1.0 | 4.0 | 6.0 | 2.0 |
| Silicate | 1.0 | 7.0 | 3.0 | 3.0 |
| CMC | 1.0 | 1.0 | 0.5 | 0.6 |
| Brightener 1 | 0.2 | 0.2 | 0.2 | 0.2 |
| Silicone antifoam | 1.0 | 1.0 | 1.0 | 0.3 |
| DTPMP | 0.4 | 0.4 | 0.2 | 0.4 |
| Spray on | | | | |
| Brightener | 0.02 | — | — | 0.02 |
| C45E7 | — | — | — | 5.0 |
| C45E2 | 2.5 | 2.5 | 2.0 | — |
| C45E3 | 2.6 | 2.5 | 2.0 | — |
| Perfume | 0.5 | 0.3 | 0.5 | 0.2 |
| Silicone antifoam | 0.3 | 0.3 | 0.3 | — |
| Dry additives | | | | |
| QEA | — | — | — | 1.0 |
| EDDS | 0.3 | — | — | — |
| Sulfate | 2.0 | 3.0 | 5.0 | 10.0 |
| Carbonate | 6.0 | 13.0 | 11.0 | 14.0 |
| Citric acid | 2.5 | — | — | 2.0 |
| QAS II | 0.5 | — | — | 0.5 |
| SKS-6 | 10.0 | — | — | — |
| Percarbonate | 18.5 | — | — | — |
| PB4 | — | 18.0 | 10.0 | 21.5 |
| TAED | 2.0 | 2.0 | — | 2.0 |
| NAC-OBS | 3.0 | 2.0 | 4.0 | — |
| Protease | 1.0 | 1.0 | 1.0 | 1.0 |
| Lipase | — | 0.4 | — | 0.2 |
| Lipase (1) | 0.4 | — | 0.4 | — |
| Amylase | 0.2 | 0.2 | 0.2 | 0.4 |
| Brightener 1 | 0.05 | — | — | 0.05 |
| PARP3 | 1.2(c) | 1.5(c) | 2.0(c) | 1.0(c) |
| Misc/minor to 100% | | | | |

EXAMPLE 4

The following granular detergent formulations were prepared in accord with the invention.

|  | A | B | C | D | E | F |
|---|---|---|---|---|---|---|
| Blown powder | | | | | | |
| LAS | 23.0 | 8.0 | 7.0 | 9.0 | 7.0 | 7.0 |
| TAS | — | — | — | — | 1.0 | — |
| C45AS | 6.0 | 6.0 | 5.0 | 8.0 | — | — |
| C45AES | — | 1.0 | 1.0 | 1.0 | — | — |
| C45E35 | — | — | — | — | 2.0 | 4.0 |
| Zeolite A | 10.0 | 18.0 | 14.0 | 12.0 | 10.0 | 10.0 |
| MA/AA | — | 0.5 | — | — | — | 2.0 |
| MA/AA (1) | 7.0 | — | — | — | — | — |
| AA | — | 3.0 | 3.0 | 2.0 | 3.0 | 3.0 |
| Sulfate | 5.0 | 6.3 | 14.3 | 11.0 | 15.0 | 19.3 |
| Silicate | 10.0 | 1.0 | 1.0 | 1.0 | 1.0 | 1.0 |
| Carbonate | 13.0 | 19.0 | 8.0 | 20.7 | 8.0 | 6.0 |
| PEG 4000 | 0.4 | 1.5 | 1.5 | 1.0 | 1.0 | 1.0 |
| DTPA | — | 0.9 | 0.5 | — | — | 0.5 |
| Brightener 2 | 0.3 | 0.2 | 0.3 | — | 0.1 | 0.3 |
| Spray on | | | | | | |
| C45E7 | — | 2.0 | — | — | 2.0 | 2.0 |
| C25E9 | 3.0 | — | — | — | — | — |
| C23E9 | — | — | 1.5 | 2.0 | — | 2.0 |
| Perfume | 0.3 | 0.3 | 0.3 | 2.0 | 0.3 | 0.3 |
| Agglomerates | | | | | | |
| C45AS | — | 5.0 | 5.0 | 2.0 | — | 5.0 |
| LAS | — | 2.0 | 2.0 | — | — | 2.0 |
| Zeolite A | — | 7.5 | 7.5 | 8.0 | — | 7.5 |
| Carbonate | — | 4.0 | 4.0 | 5.0 | — | 4.0 |
| PEG 4000 | — | 0.5 | 0.5 | — | — | 0.5 |
| Misc (water etc) | — | 2.0 | 2.0 | 2.0 | — | 2.0 |
| Dry additives | | | | | | |
| QAS (I) | — | — | — | — | 1.0 | — |
| Citric acid | — | — | — | — | 2.0 | — |
| PB4 | — | — | — | — | 12.0 | 1.0 |
| PB1 | 4.0 | 1.0 | 3.0 | 2.0 | — | — |
| Percarbonate | — | — | — | — | 2.0 | 10.0 |
| Carbonate | — | 5.3 | 1.8 | — | 4.0 | 4.0 |
| NOBS | 4.0 | — | 6.0 | — | — | 0.6 |
| Methyl cellulose | 0.2 | — | — | — | — | — |
| SKS-6 | 8.0 | — | — | — | — | — |
| STS | — | — | 2.0 | — | 1.0 | — |
| Cumene sulfonic acid | — | 1.0 | — | — | — | 2.0 |
| Lipase | 0.2 | — | 0.2 | — | 0.2 | 0.4 |
| Cellulase | 0.2 | 0.2 | 0.2 | 0.3 | 0.2 | 0.2 |
| Amylase | 0.2 | — | 0.1 | — | 0.2 | — |
| Protease | 0.5 | 0.5 | 0.5 | 0.3 | 0.5 | 0.5 |
| PVPVI | — | — | — | — | 0.5 | 0.1 |
| PVP | — | — | — | — | 0.5 | — |
| PVNO | — | — | 0.5 | 0.3 | — | — |
| QEA | — | — | — | — | 1.0 | — |
| SRP1 | 0.2 | 0.5 | 0.3 | — | 0.2 | — |
| PARP3 | 1.2(c) | 1.0(c) | 3.0(c) | 1.5(c) | 1.3(c) | 0.5(c) |
| Silicone antifoam | 0.2 | 0.4 | 0.2 | 0.4 | 0.1 | — |
| Mg sulfate | — | — | 0.2 | — | 0.2 | — |
| Misc/minors to 100% | | | | | | |

|  | G | H | I | J |
|---|---|---|---|---|
| Blown powder | | | | |
| Clay I or II | | 7.0 | 10.0 | 6.0 | 2.0 |
| LAS | 16.0 | 5.0 | 11.0 | 6.0 |
| TAS | — | 5.0 | — | 2.0 |
| Zeolite A | — | 20.0 | — | 10.0 |
| STPP | 24.0 | — | 14.0 | — |
| Sulfate | — | 2.0 | — | — |
| MA/AA | — | 2.0 | 1.0 | 1.0 |
| Silicate | 4.0 | 7.0 | 3.0 | — |
| CMC | 1.0 | — | 0.5 | 0.6 |
| Brightener 1 | 0.2 | 0.2 | 0.2 | 0.2 |
| Carbonate | 10.0 | 10.0 | 20.0 | — |
| DTPMP | 0.4 | 0.4 | 0.2 | — |
| Spray on | | | | |
| Brightener 1 | 0.02 | — | — | 0.02 |
| C45E7 or E9 | — | — | 2.0 | 1.0 |
| E45E3 or E4 | — | — | 2.0 | 4.0 |
| Perfume | 0.5 | — | 0.5 | 0.2 |
| Silicone antifoam | 0.3 | — | — | — |
| Dry additives | | | | |
| Flocculating agent I or II | 0.3 | 1.0 | 1.0 | 0.5 |
| QEA | — | — | — | 1.0 |
| HEDP/EDDS | 0.3 | — | — | — |
| Sulfate | 2.0 | — | — | — |
| Carbonate | 20.0 | 13.0 | 15.0 | 24.0 |
| Citric acid | 2.5 | — | — | 2.0 |
| QAS | — | — | 0.5 | 0.5 |
| NaSKS-6 | 3.5 | — | — | 5.0 |
| Percarbonate | — | — | — | 9.0 |
| PB4 | — | — | 5.0 | — |
| NOBS | — | — | — | 1.3 |
| TAED | — | — | 2.0 | 1.5 |
| Protease | 1.0 | 1.0 | 1.0 | 1.0 |
| Lipase | — | 0.4 | — | 0.2 |
| Amylase | 0.2 | 0.2 | 0.2 | 0.4 |
| Brightener 2 | 0.05 | — | — | 0.05 |
| Perfume | 1.0 | 0.2 | 0.5 | 0.3 |
| Speckle | 1.2 | 0.5 | 2.0 | — |
| PARP2 | 1.0 | 0.5 | 1.4 | 2.0 |
| Misc/minor to 100% | | | | |

EXAMPLE 5

The following nil bleach-containing detergent formulations of particular use in the washing of coloured clothing, according to the present invention were prepared:

|  | A | B | C |
|---|---|---|---|
| Blown Powder | | | |
| Zeolite A | 15.0 | 15.0 | — |
| Sulfate | 0.0 | 5.0 | — |
| LAS | 3.0 | 3.0 | — |
| DTPMP | 0.4 | 0.5 | — |
| CMC | 0.4 | 0.4 | — |
| MA/AA | 4.0 | 4.0 | — |
| Agglomerates | | | |
| C45AS | — | — | 11.0 |
| LAS | 6.0 | 5.0 | — |
| TAS | 3.0 | 2.0 | — |
| Silicate | 4.0 | 4.0 | — |
| Zeolite A | 10.0 | 15.0 | 13.0 |
| CMC | — | — | 0.5 |
| MA/AA | — | — | 2.0 |
| Carbonate | 9.0 | 7.0 | 7.0 |
| Spray On | | | |
| Perfume | 0.3 | 0.3 | 0.5 |
| C45E7 | 4.0 | 4.0 | 4.0 |
| C25E3 | 2.0 | 2.0 | 2.0 |
| Dry additives | | | |
| MA/AA | — | — | 3.0 |
| NaSKS-6 | — | — | 12.0 |
| Citrate | 10.0 | — | 8.0 |
| Bicarbonate | 7.0 | 3.0 | 5.0 |
| Carbonate | 6.0 | — | 7.0 |
| PVPVI/PVNO | 0.5 | 0.5 | 0.5 |
| Alcalase | 0.5 | 0.3 | 0.9 |
| Lipase | 0.4 | 0.4 | 0.4 |

|  | A | B | C |
|---|---|---|---|
| Amylase | 0.6 | 0.6 | 0.6 |
| Cellulase | 0.6 | 0.6 | 0.6 |
| PARP1 | 3.0(c) | 2.0(c) | 4.5(c) |
| Silicone antifoam | 5.0 | 5.0 | 5.0 |
| Sulfate | 0.0 | 9.0 | 0.0 |
| Misc/minors to 100% | 100.0 | 100.0 | 100.0 |
| Density (g/liter) | 700 | 700 | 700 |

EXAMPLE 6

The following granular detergent formulations were prepared in accord with the invention.

|  | A | B | C | D |
|---|---|---|---|---|
| Base granule |  |  |  |  |
| Zeolite A | 30.0 | 22.0 | 24.0 | 10.0 |
| Sulfate | 10.0 | 5.0 | 10.0 | 7.0 |
| MA/AA | 3.0 | — | — | — |
| AA | — | 1.6 | 2.0 | — |
| MA/AA (1) | — | 12.0 | — | 6.0 |
| LAS | 14.0 | 10.0 | 9.0 | 20.0 |
| C45AS | 8.0 | 7.0 | 9.0 | 7.0 |
| C45AES | — | 1.0 | 1.0 | — |
| Silicate | — | 1.0 | 0.5 | 10.0 |
| Soap | — | 2.0 | — | — |
| Brightener 1 | 0.2 | 0.2 | 0.2 | 0.2 |
| Carbonate | 6.0 | 9.0 | 10.0 | 10.0 |
| PEG 4000 | — | 1.0 | 1.5 | — |
| DTPA | — | 0.4 | — | — |
| Spray on |  |  |  |  |
| C25E9 | — | — | — | 5.0 |
| C45E7 | 1.0 | 1.0 | — | — |
| C23E9 | — | 1.0 | 2.5 | — |
| Perfume | 0.2 | 0.3 | 0.3 | — |
| Dry additives |  |  |  |  |
| Carbonate | 5.0 | 5.0 | 15.0 | 6.0 |
| PVPVI/PVNO | 0.5 | — | 0.3 | — |
| Protease | 1.0 | 1.0 | 1.0 | 0.5 |
| Lipase | 0.4 | — | — | 0.4 |
| Amylase | 0.1 | — | — | 0.1 |
| Cellulase | 0.1 | 0.2 | 0.2 | 0.1 |
| NOBS | — | 4.0 | — | 4.5 |
| PB1 | 1.0 | 5.0 | 1.5 | 6.0 |
| Sulfate | 4.0 | 5.0 | — | 5.0 |
| SRPI | — | 0.4 | — | — |
| PARP1 | 5.0(c) | 2.0(c) | 4.0(c) | — |
| PARP3 | — | 1.0(s) | — | 2.0(c) |
| Sud supressor | — | 0.5 | 0.5 | — |
| Misc/minor to 100% |  |  |  |  |

EXAMPLE 7

The following granular detergent compositions were prepared in accord with the invention.

|  | A | B | C |
|---|---|---|---|
| Blown powder |  |  |  |
| Zeolite A | 20.0 | — | 15.0 |
| STPP | — | 20.0 | — |
| Sulphate | — | — | 5.0 |
| Carbonate | — | — | 5.0 |
| TAS | — | — | 1.0 |
| LAS | 6.0 | 6.0 | 6.0 |
| C68AS | 2.0 | 2.0 | — |
| Silicate | 3.0 | 8.0 | — |
| MA/AA | 4.0 | 2.0 | 2.0 |
| CMC | 0.6 | 0.6 | 0.2 |
| Brightener 1 | 0.2 | 0.2 | 0.1 |
| DTPMP | 0.4 | 0.4 | 0.1 |
| STS | — | — | 1.0 |
| Spray on |  |  |  |
| C45E7 | 5.0 | 5.0 | 4.0 |
| Silicone antifoam | 0.3 | 0.3 | 0.1 |
| Perfume | 0.2 | 0.2 | 0.3 |
| Dry additives |  |  |  |
| QEA | — | — | 1.0 |
| Carbonate | 14.0 | 9.0 | 10.0 |
| PB1 | 1.5 | 2.0 | — |
| PB4 | 18.5 | 13.0 | 13.0 |
| TAED | 2.0 | 2.0 | 2.0 |
| QAS (l) | — | — | 1.0 |
| Photoactivated bleach | 15 ppm | 15 ppm | 15 ppm |
| SKS-6 | — | — | 3.0 |
| Protease | 1.0 | 1.0 | 0.2 |
| Lipase | 0.2 | 0.2 | 0.2 |
| Amylase | 0.4 | 0.4 | 0.2 |
| Cellulase | 0.1 | 0.1 | 0.2 |
| Sulfate | 10.0 | 20.0 | 5.0 |
| PARP4 | 1.2(c) | 2.0(c) | 1(c) |
| Misc/minors to 100% |  |  |  |
| Density (g/liter) | 700 | 700 | 700 |

EXAMPLE 8

The following detergent compositions, according to the present invention were prepared:

|  | A | B | C |
|---|---|---|---|
| Blown Powder |  |  |  |
| Zeolite A | 15.0 | 15.0 | 15.0 |
| Sulfate | 0.0 | 5.0 | 0.0 |
| LAS | 3.0 | 3.0 | 3.0 |
| QAS | — | 1.5 | 1.5 |
| DTPMP | 0.4 | 0.2 | 0.4 |
| EDDS | — | 0.4 | 0.2 |
| CMC | 0.4 | 0.4 | 0.4 |
| MA/AA | 4.0 | 2.0 | 2.0 |
| Agglomerates |  |  |  |
| LAS | 5.0 | 5.0 | 5.0 |
| TAS | 2.0 | 2.0 | 1.0 |
| Silicate | 3.0 | 3.0 | 4.0 |
| Zeolite A | 8.0 | 8.0 | 8.0 |
| Carbonate | 8.0 | 8.0 | 4.0 |
| Spray On |  |  |  |
| Perfume | 0.3 | 0.3 | 0.3 |
| C45E7 | 2.0 | 2.0 | 2.0 |
| C25E3 | 2.0 | — | — |
| Dry additives |  |  |  |
| Citrate | 5.0 | — | 2.0 |
| Bicarbonate | — | 3.0 | — |
| Carbonate | 8.0 | 15.0 | 10.0 |
| TAED | 6.0 | 2.0 | 5.0 |
| PB1 | 14.0 | 7.0 | 10.0 |

-continued

|  |  |  |  |
|---|---|---|---|
| PEO | — | — | 0.2 |
| PARP3 | 1.2(c) | 1.0(c) | 0.75(c) |
| Bentonite clay | — | — | 10.0 |
| Protease | 1.0 | 1.0 | 1.0 |
| Lipase | 0.4 | 0.4 | 0.4 |
| Amylase | 0.6 | 0.6 | 0.6 |
| Cellulase | 0.6 | 0.6 | 0.6 |
| Silicone antifoam | 5.0 | 5.0 | 5.0 |
| Sodium sulfate | 0.0 | 3.0 | 0.0 |
| Misc/minors to 100% | 100.0 | 100.0 | 100.0 |
| Density (g/liter) | 850 | 850 | 850 |

|  | D | E | F | G | H |
|---|---|---|---|---|---|
| Blown Powder |  |  |  |  |  |
| STPP/Zeolite A | 9.0 | 15.0 | 15.0 | 9.0 | 9.0 |
| Flocculating agent II or III | 0.5 | 0.2 | 0.9 | 1.5 | — |
| LAS | 7.5 | 23.0 | 3.0 | 7.5 | 7.5 |
| QAS | 2.5 | 1.5 | — | — | — |
| DTPMP | 0.4 | 0.2 | 0.4 | 0.4 | 0.4 |
| HEDP or EDDS | — | 0.4 | 0.2 | — | — |
| CMC | 0.1 | 0.4 | 0.4 | 0.1 | 0.1 |
| Sodium carbonate | 5.0 | 20.0 | 20.0 | 10.0 | — |
| Brightener | 0.05 | — | — | 0.05 | 0.05 |
| Clay I or II | — | 10.0 | — | — | — |
| STS | 0.5 | — | — | 0.5 | 0.5 |
| MA/AA | 1.5 | 2.0 | 2.0 | 1.5 | 1.5 |
| Agglomerates |  |  |  |  |  |
| Suds suppresser (silicon) | 1.0 | 1.0 | — | 2.0 | 0.5 |
| Agglomerate |  |  |  |  |  |
| Clay | 9.0 | — | — | 4.0 | 10.0 |
| Wax | 0.5 | — | — | 0.5 | 1.5 |
| Glycerol | 0.5 | — | — | 0.5 | 0.5 |
| Agglomerate |  |  |  |  |  |
| LAS | — | 5.0 | 5.0 | — | — |
| TAS | — | 2.0 | 1.0 | — | — |
| Silicate | — | 3.0 | 4.0 | — | — |
| Zeolite A | — | 8.0 | 8.0 | — | — |
| Carbonate | — | 8.0 | 4.0 | — | — |
| Spray On |  |  |  |  |  |
| Perfume | 0.3 | — | — | 0.3 | 0.3 |
| C45E7 or E9 | 2.0 | — | — | 2.0 | 2.0 |
| C25E3 or E4 | 2.0 | — | — | 2.0 | 2.0 |
| Dry additives |  |  |  |  |  |
| Citrate or citric acid | 2.5 | — | 2.0 | 2.5 | 2.5 |
| Clay I or II | — | 5.0 | 5.0 | — | — |
| Flocculating agent I or II | — | — | — | — | 0.2 |
| Bicarbonate | — | 3.0 | — | — | — |
| Carbonate | 15.0 | — | — | 25.0 | 31.0 |
| TAED | 1.0 | 2.0 | 5.0 | 1.0 | — |
| Sodium perborate or percarbonate | 6.0 | 7.0 | 10.0 | 6.0 | — |
| SRP1, 2, 3 or 4 | 0.2 | 0.1 | 0.2 | 0.5 | 0.3 |
| CMC or nonionic cellulose ether | 1.0 | 1.5 | 0.5 | — | — |
| Protease | 0.3 | 1.0 | 1.0 | 0.3 | 0.3 |
| Lipase | — | 0.4 | 0.4 | — | — |
| Amylase | 0.2 | 0.6 | 0.6 | 0.2 | 0.2 |
| Cellulase | 0.2 | 0.6 | 0.6 | 0.2 | 0.2 |
| Silicone antifoam | — | 5.0 | 5.0 | — | — |
| Perfume (starch) | 0.2 | 0.3 | 1.0 | 0.2 | 0.2 |
| Speckle | 0.5 | 0.5 | 0.1 | — | 1.0 |
| NaSKS-6 (silicate 2R) | 3.5 | — | — | — | 3.5 |
| Photobleach | 0.1 | — | — | 0.1 | 0.1 |
| Soap | 0.5 | 2.5 | — | 0.5 | 0.5 |
| Sodium sulfate | — | 3.0 | — | — | — |
| PARP2 | 0.7 | 1.0 | 2.0 | 0.4 | 1.5 |

-continued

|  | | | | | |
|---|---|---|---|---|---|
| Misc/minors to 100% | 100.0 | 100.0 | 100.0 | 100.0 | 100.0 |
| Density (g/liter) | 850 | 850 | 850 | 850 | 850 |

EXAMPLE 9

The following detergent formulations, according to the present invention were prepared:

|  | A | B | C | D |
|---|---|---|---|---|
| LAS | 18.0 | 14.0 | 24.0 | 20.0 |
| QAS | 0.7 | 1.0 | — | 0.7 |
| TFAA | — | 1.0 | — | — |
| C23E56.5 | — | — | 1.0 | — |
| C45E7 | — | 1.0 | — | — |
| C45E3S | 1.0 | 2.5 | 1.0 | — |
| STPP | 32.0 | 18.0 | 30.0 | 22.0 |
| Silicate | 9.0 | 5.0 | 9.0 | 8.0 |
| Carbonate | 9.0 | 7.5 | — | 5.0 |
| Bicarbonate | — | 7.5 | — | — |
| PB1 | 3.0 | 1.0 | — | — |
| PB4 | — | 1.0 | — | — |
| NOBS | 2.0 | 1.0 | — | — |
| DTPMP | — | 1.0 | — | — |
| DTPA | 0.5 | — | 0.2 | 0.3 |
| SRP 1 | 0.3 | 0.2 | — | 0.1 |
| MA/AA | 1.0 | 1.5 | 2.0 | 0.5 |
| CMC | 0.8 | 0.4 | 0.4 | 0.2 |
| PEI | — | — | 0.4 | — |
| Sodium sulfate | 20.0 | 10.0 | 20.0 | 30.0 |
| Mg sulfate | 0.2 | — | 0.4 | 0.9 |
| Protease | 0.8 | 1.0 | 0.5 | 0.5 |
| Amylase | 0.5 | 0.4 | — | 0.25 |
| Lipase | 0.2 | — | 0.1 | — |
| Cellulase | 0.15 | — | — | 0.05 |
| Photoactivated bleach (ppm) | 30 ppm | 20 ppm | — | 10 ppm |
| PARP4 | 2.0(c) | 1(c) | 0.8(c) | 2(c) |
| Perfume spray on | 0.3 | 0.3 | 0.1 | 0.2 |
| Brightener 1/2 | 0.05 | 0.2 | 0.08 | 0.1 |
| Misc/minors to 100% |  |  |  |  |

EXAMPLE 10

The following is a composition in the form of a tablet, bar, extrudate or granule in accord with the invention.

|  | A | B | C | D | E | F | G |
|---|---|---|---|---|---|---|---|
| Sodium $C_{11}$–$C_{13}$ alkylbenzenesulfonate | 12.0 | 16.0 | 23.0 | 19.0 | 18.0 | 20.0 | 16.0 |
| Sodium $C_{14}$–$C_{15}$ alcohol sulfate | — | 4.5 | — | — | — | — | 4.0 |
| $C_{14}$–$C_{15}$ alcohol ethoxylate (3) sulfate | — | — | 2.0 | — | 1.0 | 1.0 | 1.0 |
| Sodium $C_{14}$–$C_{15}$ alcohol ethoxylate | 2.0 | 2.0 | — | 1.3 | — | — | 5.0 |
| $C_9$–$C_{14}$ alkyl dimethyl hydroxy ethyl quaternary ammonium salt | — | — | — | — | 1.0 | 0.5 | 2.0 |
| Tallow fatty acid | — | — | — | — | — | — | 1.0 |
| Sodium tripolyphosphate/ Zeolite | 23.0 | 25.0 | 14.0 | 22.0 | 20.0 | 10.0 | 20.0 |

-continued

| | | | | | | | |
|---|---|---|---|---|---|---|---|
| Sodium carbonate | 25.0 | 22.0 | 35.0 | 20.0 | 28.0 | 41.0 | 30.0 |
| Sodium Polyacrylate (45%) | 0.5 | 0.5 | 0.5 | 0.5 | — | — | — |
| Sodium polyacrylate/maleate polymer | — | — | 1.0 | 1.0 | 1.0 | 2.0 | 0.5 |
| Sodium silicate (1:6 ratio NaO/SiO$_2$)(46%) | 3.0 | 6.0 | 9.0 | 8.0 | 9.0 | 6.0 | 8.0 |
| Sodium sulfate | — | — | — | — | — | 2.0 | 3.0 |
| Sodium perborate/percarbonate | 5.0 | 5.0 | 10.0 | — | 3.0 | 1.0 | — |
| Poly(ethyleneglycol), MW ~4000 (50%) | 1.5 | 1.5 | 1.0 | 1.0 | — | — | 0.5 |
| Sodium carboxy methyl cellulose | 1.0 | 1.0 | 1.0 | — | 0.5 | 0.5 | 0.5 |
| NOBS/DOBS | — | 1.0 | — | — | 1.0 | 0.7 | — |
| TAED | 1.5 | 1.0 | 2.5 | — | 3.0 | 0.7 | — |
| SRP 1 | 1.5 | 1.5 | 1.0 | 1.0 | — | 1.0 | — |
| Clay I or II | 5.0 | 6.0 | 12.0 | 7.0 | 10.0 | 4.0 | 3.0 |
| Flocculating agent I or III | 0.2 | 0.2 | 3.0 | 2.0 | 0.1 | 1.0 | 0.5 |
| Humectant | 0.5 | 1.0 | 0.5 | 1.0 | 0.5 | 0.5 | — |
| Wax | 0.5 | 0.5 | 1.0 | — | — | 0.5 | 0.5 |
| Moisture | 7.5 | 7.5 | 6.0 | 7.0 | 5.0 | 3.0 | 5.0 |
| Magnesium sulphate | — | — | — | — | — | 0.5 | 1.5 |
| Chelant | — | — | — | — | 0.8 | 0.6 | 1.0 |
| Enzymes, including amylase, cellulase, protease and lipase | — | — | — | — | 2.0 | 1.5 | 2.0 |
| Speckle | 2.5 | 4.1 | 4.2 | 4.4 | 5.6 | 5.0 | 5.2 |
| minors, e.g. perfume, PVP, PVPVI/PVNO, brightener, photobleach, | 2.0 | 1.0 | 1.0 | 1.0 | 2.5 | 1.5 | 1.0 |
| PARP2 | 1.6 | 2.0 | 0.4 | 2.0 | 1.0 | 1.6 | 0.5 |

| | H | I | J | K |
|---|---|---|---|---|
| Sodium C$_{11}$–C$_{13}$ alkylbenzenesulfonate | 23.0 | 13.0 | 20.0 | 18.0 |
| Sodium C$_{14}$–C$_{15}$ alcohol sulfate | — | 4.0 | — | — |
| Clay I or II | 5.0 | 10.0 | 14.0 | 6.0 |
| Flocculating agent I or II | 0.2 | 0.3 | 0.1 | 0.9 |
| Wax | 0.5 | 0.5 | 1.0 | — |
| Humectant (glycerol/silica) | 0.5 | 2.0 | 1.5 | — |
| C$_{14}$–C$_{15}$ alcohol ethoxylate sulfate | — | — | — | 2.0 |
| Sodium C$_{14}$–C$_{15}$ alcohol ethoxylate ( | 2.5 | 3.5 | — | — |
| C$_9$–C$_{14}$ alkyl dimethyl hydroxy ethyl quaternary ammonium salt | — | — | — | 0.5 |
| Tallow fatty acid | 0.5 | — | — | — |
| Tallow alcohol ethoxylate (50) | — | — | — | 1.3 |
| Sodium tripolyphosphate | — | 41.0 | — | 20.0 |
| Zeolite A, hydrate (0.1–10 micron size) | 26.3 | — | 21.3 | — |
| Sodium carbonate | 24.0 | 22.0 | 35.0 | 27.0 |
| Sodium Polyacrylate (45%) | 2.4 | — | 2.7 | — |
| Sodium polyacylate/maleate polymer | — | — | 1.0 | 2.5 |
| Sodium silicate (1.6 or 2 or 2.2 ratio NaO/SiO$_2$)(46%) | 4.0 | 7.0 | 2.0 | 6.0 |
| Sodium sulfate | — | 6.0 | 2.0 | — |
| Sodium perborate/percarbonate | 8.0 | 4.0 | — | 12.0 |
| Poly(ethyleneglycol), MW ~4000 (50%) | 1.7 | 0.4 | 1.0 | — |
| Sodium carboxy methyl cellulose | 1.0 | — | — | 0.3 |
| Citric acid | — | — | 3.0 | — |
| NOBS/DOBS | 1.2 | — | — | 1.0 |
| TAED | 0.6 | 1.5 | — | 3.0 |
| Perfume | 0.5 | 1.0 | 0.3 | 0.4 |
| SRP 1 | — | 1.5 | 1.0 | 1.0 |
| Moisture | 7.5 | 3.1 | 6.1 | 7.3 |
| Magnesium sulphate | — | — | — | 1.0 |
| Chelant | — | — | — | 0.5 |
| speckle | 1.0 | 0.5 | 0.2 | 2.7 |
| Enzymes, including amylase, cellulase, protease and lipase | — | 1.0 | — | 1.5 |
| minors, e.g. brightener, photo-bleach | 1.0 | 1.0 | 1.0 | 1.0 |
| PARP3 | 1.2 | 0.4 | 1.6 | 2.0 |

EXAMPLE 11

The following liquid detergent formulations were prepared in accord with the invention (levels are given as parts per weight).

| | A | B | C | D | E |
|---|---|---|---|---|---|
| LAS | 11.5 | 8.8 | — | 3.9 | — |
| C25E2.5S | — | 3.0 | 18.0 | — | 16.0 |
| C45E2.25S | 11.5 | 3.0 | — | 15.7 | — |
| C23E9 | — | 2.7 | 1.8 | 2.0 | 1.0 |
| C23E7 | 3.2 | — | — | — | — |
| CFAA | — | — | 5.2 | — | 3.1 |
| TPKFA | 1.6 | — | 2.0 | 0.5 | 2.0 |
| Citric acid 50% | 6.5 | 1.2 | 2.5 | 4.4 | 2.5 |
| Calcium formate | 0.1 | 0.06 | 0.1 | — | — |
| Sodium formate | 0.5 | 0.06 | 0.1 | 0.05 | 0.05 |
| Sodium cumene sulfonate | 4.0 | 1.0 | 3.0 | 1.18 | — |
| Borate | 0.6 | — | 3.0 | 2.0 | 2.9 |
| Sodium hydroxide | 5.8 | 2.0 | 3.5 | 3.7 | 2.7 |
| Ethanol | 1.75 | 1.0 | 3.6 | 4.2 | 2.9 |
| 1,2 propanediol | 3.3 | 2.0 | 8.0 | 7.9 | 5.3 |
| Monoethanolamine | 3.0 | 1.5 | 1.3 | 2.5 | 0.8 |
| TEPAE | 1.6 | — | 1.3 | 1.2 | 1.2 |
| Protease | 1.0 | 0.3 | 1.0 | 0.5 | 0.7 |
| Lipase | — | — | 0.1 | — | — |
| Cellulase | — | — | 0.1 | 0.2 | 0.05 |
| Amylase | — | — | — | 0.1 | — |
| SRP1 | 0.2 | — | 0.1 | — | — |
| DTPA | — | — | 0.3 | — | — |
| PVNO | — | — | 0.3 | — | 0.2 |
| PARP1 | 2.0(c) | — | — | — | — |
| PARP2 | — | 0.8 | — | — | — |
| PARP3 | — | — | 1.0(c) | — | 2.0(c) |
| PARP4 | — | — | — | 1.4(c) | — |
| Brightener 1 | 0.2 | 0.07 | 0.1 | — | — |
| Silicone antifoam | 0.04 | 0.02 | 0.1 | 0.1 | 0.1 |
| Water/minors up to 100% | | | | | |

EXAMPLE 12

The following liquid detergent formulations were prepared in accord with the invention (levels are given in parts per weight):

| | A | B | C | D | E | F | G | H |
|---|---|---|---|---|---|---|---|---|
| LAS | 10.0 | 13.0 | 9.0 | — | 25.0 | — | — | — |
| C25AS | 4.0 | 1.0 | 2.0 | 10.0 | — | 13.0 | 18.0 | 15.0 |
| C25E3S | 1.0 | — | — | 3.0 | — | 2.0 | 2.0 | 4.0 |
| C25E7 | 6.0 | 8.0 | 13.0 | 2.5 | — | 4.0 | 4.0 | 4.0 |
| TFAA | — | — | — | 4.5 | — | 6.0 | 8.0 | 8.0 |
| APA | — | 1.4 | — | — | 3.0 | 1.0 | 2.0 | — |
| TPKFA | 2.0 | — | 13.0 | 7.0 | — | 15.0 | 11.0 | 11.0 |
| Citric acid | 2.0 | 3.0 | 1.0 | 1.5 | 1.0 | 1.0 | 1.0 | 1.0 |
| Dodecenyl/tetradecenyl succinic acid | 12.0 | 10.0 | — | — | 15.0 | — | — | — |
| Rape seed fatty acid | 4.0 | 2.0 | 1.0 | — | 1.0 | — | 3.5 | — |
| Ethanol | 4.0 | 4.0 | 7.0 | 2.0 | 7.0 | 2.0 | 3.0 | 2.0 |
| 1,2 Propanediol | 4.0 | 4.0 | 2.0 | 7.0 | 6.0 | 8.0 | 10.0 | 13.0 |
| Monoethanolamine | — | — | — | 5.0 | — | — | 9.0 | 9.0 |

-continued

|  | A | B | C | D | E | F | G | H |
|---|---|---|---|---|---|---|---|---|
| Tri-ethanolamine | — | — | 8.0 | — | — | — | — | — |
| TEPAE | 0.5 | — | 0.5 | 0.2 | — | — | 0.4 | 0.3 |
| DTPMP | 1.0 | 1.0 | 0.5 | 1.0 | 2.0 | 1.2 | 1.0 | — |
| Protease | 0.5 | 0.5 | 0.4 | 0.25 | — | 0.5 | 0.3 | 0.6 |
| Alcalase | — | — | — | — | 1.5 | — | — | — |
| Lipase | — | 0.10 | — | 0.01 | — | — | 0.15 | 0.15 |
| Amylase | 0.25 | 0.25 | 0.6 | 0.5 | 0.25 | 0.9 | 0.6 | 0.6 |
| Cellulase | — | — | — | 0.05 | — | — | 0.15 | 0.15 |
| Endolase | — | — | 0.10 | — | — | — | 0.07 | — |
| SRP2 | 0.3 | — | 0.3 | 0.1 | — | — | 0.2 | 0.1 |
| Boric acid | 0.1 | 0.2 | 1.0 | 2.0 | 1.0 | 1.5 | 2.5 | 2.5 |
| Calcium chloride | — | 0.02 | — | 0.01 | — | — | — | — |
| Bentonite clay | — | — | — | — | 4.0 | 4.0 | — | — |
| Brightener 1 | — | 0.4 | — | — | 0.1 | 0.2 | 0.3 | — |
| Sud supressor | 0.1 | 0.3 | — | 0.1 | 0.4 | — | — | — |
| Opacifier | 0.5 | 0.4 | — | 0.3 | 0.8 | 0.7 | — | — |
| PARP1(c) | 2.8 | — | 2.5 | — | 3.3 | — | 4.4 | 1.2 |
| PARP3(c) | — | 2.0 | — | 1.0 | — | 0.8 | 0.1 | 0.7 |
| Water/minors up to 100% |  |  |  |  |  |  |  |  |
| NaOH up to pH | 8.0 | 8.0 | 7.6 | 7.7 | 8.0 | 7.5 | 8.0 | 8.2 |

EXAMPLE 13

The following liquid detergent compositions were prepared in accord with the invention (levels are given in parts per weight).

|  | A | B |
|---|---|---|
| LAS | 27.6 | 18.9 |
| C45AS | 13.8 | 5.9 |
| C13E8 | 3.0 | 3.1 |
| Oleic acid | 3.4 | 2.5 |
| Citric acid | 5.4 | 5.4 |
| Sodium hydroxide | 0.4 | 3.6 |
| Calcium formate | 0.2 | 0.1 |
| Sodium formate | — | 0.5 |
| Ethanol | 7.0 | — |
| Monoethanolamine | 16.5 | 8.0 |
| 1,2 propanediol | 5.9 | 5.5 |
| Xylene sulfonic acid | — | 2.4 |
| TEPAE | 1.5 | 0.8 |
| Protease | 1.5 | 0.6 |
| PEG | — | 0.7 |
| Brightener 2 | 0.4 | 0.1 |
| Perfume spray on | 0.5 | 0.3 |
| PARP2 | 1.2 | — |
| PARP7 | 0.2 | 1.0 |
| Water/minors up to 100% |  |  |

EXAMPLE 14

The following laundry bar detergent compositions were prepared in accord with the invention (levels are given in parts per weight).

|  | A | B | C | D | E | F | G | H |
|---|---|---|---|---|---|---|---|---|
| LAS | — | — | 19.0 | 15.0 | 21.0 | 6.75 | 8.8 | — |
| C28AS | 30.0 | 13.5 | — | — | — | 15.75 | 11.2 | 22.5 |
| Sodium laurate | 2.5 | 9.0 | — | — | — | — | — | — |

-continued

|  | A | B | C | D | E | F | G | H |
|---|---|---|---|---|---|---|---|---|
| Zeolite A | 2.0 | 1.25 | — | — | — | 1.25 | 1.25 | 1.25 |
| Carbonate | 10.0 | — | 11.0 | 5.0 | 2.0 | 7.0 | 13.0 | 9.0 |
| Calcium carbonate | 27.5 | 39.0 | 35.0 | — | — | 40.0 | — | 40.0 |
| Sulfate | 5.0 | 5.0 | 3.0 | 5.0 | 3.0 | — | — | 5.0 |
| TSPP | 5.0 | — | — | — | — | 5.0 | 2.5 | — |
| STPP | 5.0 | 15.0 | 10.0 | — | — | 7.0 | 8.0 | 10.0 |
| Bentonite clay | — | 10.0 | — | — | 5.0 | — | — | — |
| DTPMP | — | 0.7 | 0.6 | — | 0.6 | 0.7 | 0.7 | 0.7 |
| CMC | — | 1.0 | 1.0 | 1.0 | 1.0 | — | — | 1.0 |
| Talc | — | — | 10.0 | 15.0 | 10.0 | — | — | — |
| Silicate | — | — | 4.0 | 5.0 | 3.0 | — | — | — |
| PVNO | 0.02 | 0.03 | — | 0.01 | — | 0.02 | — | — |
| MA/AA | 0.4 | 1.0 | — | — | 0.2 | 0.4 | 0.5 | 0.4 |
| SRP1 | 0.3 | 0.3 | 0.3 | 0.3 | 0.3 | 0.3 | 0.3 | 0.3 |
| Protease | — | 0.12 | — | 0.08 | 0.08 | — | — | 0.1 |
| Lipase | — | 0.1 | — | 0.1 | — | — | — | — |
| Amylase | — | — | 0.8 | — | — | — | 0.1 | — |
| Cellulase | — | 0.15 | — | — | 0.15 | 0.1 | — | — |
| PEO | — | 0.2 | — | 0.2 | 0.3 | — | — | 0.3 |
| Perfume | 1.0 | 0.5 | 0.3 | 0.2 | 0.4 | — | — | 0.4 |
| Mg sulfate | — | — | 3.0 | 3.0 | 3.0 | — | — | — |
| PARP1(c) | 3.0 | — | — | — | — | 2.0 | — | — |
| PARP2 | — | 1.4 | — | — | — | — | 2.0 | — |
| PARP3(c) | — | — | 0.8 | — | — | — | — | 1.0 |
| PARP7 | — | — | — | 0.4 | 0.1 | — | — | 0.05 |
| Brightener | 0.15 | 0.10 | 0.15 | — | — | — | — | 0.1 |
| Photoactivated bleach (ppm) | — | 15.0 | 15.0 | 15.0 | 15.0 | — | — | 15.0 |

EXAMPLE 15

The following detergent additive compositions were prepared according to the present invention:

|  | A | B | C |
|---|---|---|---|
| LAS | — | 5.0 | 5.0 |
| STPP | 30.0 | — | 20.0 |
| Zeolite A | — | 35.0 | 20.0 |
| PB1 | 20.0 | 15.0 | — |
| TAED | 10.0 | 8.0 | — |
| PARP1(c) | 3.1 | — | 1.1 |
| PARP2 | — | 0.4 | 0.2 |
| Protease | — | 0.3 | 0.3 |
| Amylase | — | 0.06 | 0.06 |
| Minors, water and miscellaneous | Up to 100% |  |  |

EXAMPLE 16

The following compact high density (0.96 Kg/l) dishwashing detergent compositions were prepared according to the present invention:

|  | A | B | C | D | E | F | G | H |
|---|---|---|---|---|---|---|---|---|
| STPP | — | — | 54.3 | 51.4 | 51.4 | — | — | 50.9 |
| Citrate | 35.0 | 17.0 | — | — | — | 46.1 | 40.2 | — |
| Carbonate | — | 15.0 | 12.0 | 14.0 | 4.0 | — | 7.0 | 31.1 |
| Bicarbonate | — | — | — | — | — | 25.4 | — | — |
| Silicate | 32.0 | 14.8 | 14.8 | 10.0 | 10.0 | 1.0 | 25.0 | 3.1 |
| Metasilicate | — | 2.5 | — | 9.0 | 9.0 | — | — | — |
| PB1 | 1.9 | 9.7 | 7.8 | 7.8 | 7.8 | — | — | — |
| PB4 | 8.6 | — | — | — | — | — | — | — |
| Percarbonate | — | — | — | — | — | 6.7 | 11.8 | 4.8 |
| Nonionic | 1.5 | 2.0 | 1.5 | 1.7 | 1.5 | 2.6 | 1.9 | 5.3 |
| TAED | 5.2 | 2.4 | — | — | — | 2.2 | — | 1.4 |
| HEDP | — | 1.0 | — | — | — | — | — | — |
| DTPMP | — | 0.6 | — | — | — | — | — | — |
| MnTACN | — | — | — | — | — | — | 0.008 | — |
| PAAC | — | — | 0.008 | 0.01 | 0.007 | — | — | — |
| BzP | — | — | — | — | 1.4 | — | — | — |
| Paraffin | 0.5 | 0.5 | 0.5 | 0.5 | 0.5 | 0.6 | — | — |
| PARP3(c) | 1.2 | 1.4 | 1.2 | 1.1 | — | — | — | 0.5 |
| PARP1(c) | — | — | — | — | 2.1 | 2.3 | 4.2 | — |
| Protease | 0.072 | 0.072 | 0.029 | 0.053 | 0.046 | 0.026 | 0.059 | 0.06 |
| Amylase | 0.012 | 0.012 | 0.006 | 0.012 | 0.013 | 0.009 | 0.017 | 0.03 |
| Lipase | — | 0.001 | — | 0.005 | — | — | — | — |
| BTA | 0.3 | 0.3 | 0.3 | 0.3 | 0.3 | — | 0.3 | 0.3 |
| MA/AA | — | — | — | — | — | — | 4.2 | — |
| 480N | 3.3 | 6.0 | — | — | — | — | — | 0.9 |
| Perfume | 0.2 | 0.2 | 0.2 | 0.2 | 0.2 | 0.2 | 0.1 | 0.1 |
| Sulphate | 7.0 | 20.0 | 5.0 | 2.2 | 0.8 | 12.0 | 4.6 | — |
| pH | 10.8 | 11.0 | 10.8 | 11.3 | 11.3 | 9.6 | 10.8 | 10.9 |
| Miscellaneous and water |  |  |  | Up to 100% |  |  |  |  |

EXAMPLE 17

The following granular dishwashing detergent compositions of bulk density 1.02 Kg/L were prepared according to the present invention:

|  | A | B | C | D | E | F | G | H |
|---|---|---|---|---|---|---|---|---|
| STPP | 30.0 | 30.0 | 33.0 | 34.2 | 29.6 | 31.1 | 26.6 | 17.6 |
| Carbonate | 29.5 | 30.0 | 29.0 | 24.0 | 15.0 | 36.0 | 2.1 | 38.0 |
| Silicate | 7.4 | 7.4 | 7.5 | 7.2 | 13.3 | 3.4 | 43.7 | 12.4 |
| Metasilicate | — | — | 4.5 | 5.1 | — | — | — | — |
| Percarbonate | — | — | — | — | — | 4.0 | — | — |
| PB1 | 4.4 | 4.2 | 4.5 | 4.5 | — | — | — | — |
| NADCC | — | — | — | — | 2.0 | — | 1.6 | 1.0 |
| Nonionic | 1.2 | 1.0 | 0.7 | 0.8 | 1.9 | 0.7 | 0.6 | 0.3 |
| TAED | 1.0 | — | — | — | — | 0.8 | — | — |
| PAAC | — | 0.004 | 0.004 | 0.004 | — | — | — | — |
| BzP | — | — | — | 1.4 | — | — | — | — |
| Paraffin | 0.25 | 0.25 | 0.25 | 0.25 | — | — | — | — |
| PARP4 | 1.0(c) | 0.5(c) | 1.4(c) | 1.8(c) | — | — | 1.0(c) | 0.5(c) |
| PARP1(c) | — | — | — | — | 0.1 | 0.15 | 0.2 | 0.1 |
| Protease | 0.036 | 0.015 | 0.03 | 0.028 | — | 0.03 | — | — |
| Amylase | 0.003 | 0.003 | 0.01 | 0.006 | — | 0.01 | — | — |
| Lipase | 0.005 | — | 0.001 | — | — | — | — | — |
| BTA | 0.15 | 0.15 | 0.15 | 0.15 | — | — | — | — |
| Perfume | 0.2 | 0.2 | 0.2 | 0.2 | 0.1 | 0.2 | 0.2 | — |
| Sulphate | 23.4 | 25.0 | 22.0 | 18.5 | 30.1 | 19.3 | 23.1 | 23.6 |
| pH | 10.8 | 10.8 | 11.3 | 11.3 | 10.7 | 11.5 | 12.7 | 10.9 |
| Miscellaneous and water |  |  |  | Up to 100% |  |  |  |  |

EXAMPLE 18

The following tablet detergent compositions were prepared according to the present invention by compression of a granular dishwashing detergent composition at a pressure of 13 KN/cm² using a standard 12 head rotary press:

|  | A | B | C | D | E | F |
|---|---|---|---|---|---|---|
| STPP | — | 48.8 | 49.2 | 36.0 | — | 46.8 |
| Citrate | 26.4 | — | — | — | 31.1 | — |
| Carbonate | — | 4.0 | 12.0 | 14.4 | 10.0 | 20.0 |
| Silicate | 26.4 | 14.8 | 15.0 | 12.6 | 17.7 | 2.4 |
| PARP1(c) | 2.3 | — | — | — | 2.5 | — |
| PARP2 | — | 0.8 | — | — | — | 0.2 |
| PARP3(c) | — | — | 1.2 | 1 | — | — |
| Protease | 0.056 | 0.072 | 0.041 | 0.033 | 0.052 | 0.013 |
| Amylase | 0.01 | 0.03 | 0.012 | 0.007 | 0.016 | 0.002 |
| Lipase | 0.005 | — | — | — | — | — |
| PB1 | 1.6 | 7.7 | 12.2 | 10.6 | 15.7 | — |
| PB4 | 6.9 | — | — | — | — | 14.4 |
| Nonionic | 1.5 | 2.0 | 1.5 | 1.65 | 0.8 | 6.3 |
| PAAC | — | — | 0.02 | 0.009 | — | — |
| MnTACN | — | — | — | — | 0.007 | — |
| TAED | 4.3 | 2.5 | — | — | 1.3 | 1.8 |
| HEDP | 0.7 | — | — | 0.7 | — | 0.4 |
| DTPMP | 0.65 | — | — | — | — | — |
| Paraffin | 0.4 | 0.5 | 0.5 | 0.55 | — | — |
| BTA | 0.2 | 0.3 | 0.3 | 0.3 | — | — |
| PA30 | 3.2 | — | — | — | — | — |
| MA/AA | — | — | — | — | 4.5 | 0.55 |
| Perfume | — | — | 0.05 | 0.05 | 0.2 | 0.2 |
| Sulphate | 24.0 | 13.0 | 2.3 | — | 10.7 | 3.4 |
| Weight of tablet | 25 g | 25 g | 20 g | 30 g | 18 g | 20 g |
| pH | 10.6 | 10.6 | 10.7 | 10.7 | 10.9 | 11.2 |
| Miscellaneous and water | Up to 100% | | | | | |

EXAMPLE 19

The following liquid dishwashing detergent compositions of density 1.40 Kg/L were prepared according to the present invention:

|  | A | B | C | D |
|---|---|---|---|---|
| STPP | 17.5 | 17.5 | 17.2 | 16.0 |
| Carbonate | 2.0 | — | 2.4 | — |
| Silicate | 5.3 | 6.1 | 14.6 | 15.7 |
| NaOCl | 1.15 | 1.15 | 1.15 | 1.25 |
| Polygen/carbopol | 1.1 | 1.0 | 1.1 | 1.25 |
| Nonionic | — | — | 0.1 | — |
| NaBz | 0.75 | 0.75 | — | — |
| PARP2 | 0.4 | 0.8 | 0.1 | 0.5 |
| NaOH | — | 1.9 | — | 3.5 |
| KOH | 2.8 | 3.5 | 3.0 | — |
| pH | 11.0 | 11.7 | 10.9 | 11.0 |
| Sulphate, miscellaneous and water | up to 100% | | | |

EXAMPLE 20

The following liquid rinse aid compositions were prepared according to the present invention:

|  | A | B | C |
|---|---|---|---|
| Nonionic | 12.0 | — | 14.5 |
| Nonionic blend | — | 64.0 | — |
| Citric | 3.2 | — | 6.5 |
| HEDP | 0.5 | — | — |
| PEG | — | 5.0 | — |
| SCS | 4.8 | — | 7.0 |
| Ethanol | 6.0 | 8.0 | — |
| PARP7 | 3 | — | 1 |
| PARP3(c) | — | 0.2 | 0.1 |
| pH of the liquid | 2.0 | 7.5 | / |
| Miscellaneous and water | Up to 100% | | |

EXAMPLE 21

The following liquid dishwashing compositions were prepared according to the present invention:

|  | A | B | C | D | E |
|---|---|---|---|---|---|
| C17ES | 28.5 | 27.4 | 19.2 | 34.1 | 34.1 |
| Amine oxide | 2.6 | 5.0 | 2.0 | 3.0 | 3.0 |
| C12 glucose amide | — | — | 6.0 | — | — |
| Betaine | 0.9 | — | — | 2.0 | 2.0 |
| Xylene sulfonate | 2.0 | 4.0 | — | 2.0 | — |
| Neodol C11E9 | — | — | 5.0 | — | — |
| Polyhydroxy fatty acid amide | — | — | — | 6.5 | 6.5 |
| Sodium diethylene penta acetate (40%) | — | — | 0.03 | — | — |
| TAED | — | — | — | 0.06 | 0.06 |
| Sucrose | — | — | — | 1.5 | 1.5 |
| Ethanol | 4.0 | 5.5 | 5.5 | 9.1 | 9.1 |
| Alkyl diphenyl oxide disulfonate | — | — | — | — | 2.3 |
| Ca formate | — | — | — | 0.5 | 1.1 |
| Ammonium citrate | 0.06 | 0.1 | — | — | — |
| Na chloride | — | 1.0 | — | — | — |
| Mg chloride | 3.3 | — | 0.7 | — | — |
| Ca chloride | — | — | 0.4 | — | — |
| Na sulfate | — | — | 0.06 | — | — |
| Mg sulfate | 0.08 | — | — | — | — |
| Mg hydroxide | — | — | — | 2.2 | 2.2 |
| Na hydroxide | — | — | — | 1.1 | 1.1 |
| Hydrogen peroxide | 200 ppm | 0.16 | 0.006 | — | — |
| PARP3(c) | 0.4 | — | 1.2 | — | 0.1 |
| Protease | 0.017 | 0.005 | .0035 | 0.003 | 0.002 |
| Perfume | 0.18 | 0.09 | 0.09 | 0.2 | 0.2 |
| Water and minors | Up to 100% | | | | |

EXAMPLE 22

The following liquid hard surface cleaning compositions were prepared according to the present invention:

|  | A | B | C | D | E |
|---|---|---|---|---|---|
| PARP1(c) | 2.8 | — | 1.6 | — | 0.4 |
| PARP7(c) | — | 1.2 | — | 1.0 | 0.5 |
| Amylase | 0.01 | 0.002 | 0.005 | — | — |
| Protease | 0.05 | 0.01 | 0.02 | — | — |
| Hydrogen peroxide | — | — | — | 6.0 | 6.8 |
| Acetyl triethyl citrate | — | — | — | 2.5 | — |
| DTPA | — | — | — | 0.2 | — |
| Butyl hydroxy toluene | — | — | — | 0.05 | — |
| EDTA* | 0.05 | 0.05 | 0.05 | — | — |
| Citric/Citrate | 2.9 | 2.9 | 2.9 | 1.0 | — |

-continued

|  | A | B | C | D | E |
|---|---|---|---|---|---|
| LAS | 0.5 | 0.5 | 0.5 | — | — |
| C12 AS | 0.5 | 0.5 | 0.5 | — | — |
| C10AS | — | — | — | — | 1.7 |
| C12(E)S | 0.5 | 0.5 | 0.5 | — | — |
| C12,13 E6.5 nonionic | 7.0 | 7.0 | 7.0 | — | — |
| Neodol 23-6.5 | — | — | — | 12.0 | — |
| Dobanol 23-3 | — | — | — | — | 1.5 |
| Dobanol 91-10 | — | — | — | — | 1.6 |
| C25AE1.8S | — | — | — | 6.0 | — |
| Na paraffin sulphonate | — | — | — | 6.0 | — |
| Perfume | 1.0 | 1.0 | 1.0 | 0.5 | 0.2 |
| Propanediol | — | — | — | 1.5 | — |
| Ethoxylated tetraethylene pentaimine | — | — | — | 1.0 | — |
| 2, Butyl octanol | — | — | — | — | 0.5 |
| Hexyl carbitol** | 1.0 | 1.0 | 1.0 | — | — |
| SCS | 1.3 | 1.3 | 1.3 | — | — |
| pH adjusted to | 7–12 | 7–12 | 7–12 | 4 | — |
| Miscellaneous and water | | Up to 100% | | | |

*Na4 ethylenediamine diacetic acid
**Diethylene glycol monohexyl ether

EXAMPLE 23

The following spray composition for cleaning of hard surfaces and removing household mildew was prepared according to the present invention:

| PARP3 | 1 |
|---|---|
| Amylase | 0.01 |
| Protease | 0.01 |
| Na octyl sulfate | 2.0 |
| Na dodecyl sulfate | 4.0 |
| Na hydroxide | 0.8 |
| Silicate | 0.04 |
| Butyl carbitol* | 4.0 |
| Perfume | 0.35 |
| Water/minors | up to 100% |

*Diethylene glycol monobutyl ether

EXAMPLE 24

The following lavatory cleansing block compositions were prepared according to the present invention.

|  | A | B | C |
|---|---|---|---|
| C16-18 fatty alcohol/50EO | 70.0 | — | — |
| LAS | — | — | 80.0 |
| Nonionic | — | 1.0 | — |
| Oleoamide surfactant | — | 25.0 | — |
| Partially esterified copolymer of vinylmethyl ether and maleic anhydride, viscosity 0.1–0.5 | 5.0 | — | — |
| Polyethylene glycol MW 8000 | — | 38.0 | — |
| Water-soluble K-polyacrylate MW 4000–8000 | — | 12.0 | — |
| Water-soluble Na-copolymer of acrylamide (70%) and acrylic acid (30%) low MW | — | 19.0 | — |
| Na triphosphate | 10.0 | — | — |
| Carbonate | — | — | — |
| PARP1(c) | 1.0 | — | 1.6 |
| PARP3(s) | — | 1.2 | 0.5 |
| Dye | 2.5 | 1.0 | 1.0 |
| Perfume | 3.0 | — | 7.0 |
| KOH/HCL solution | | pH 6–11 | |

EXAMPLE 25

The following toilet bowl cleaning composition was prepared according to the present invention.

|  | A | B |
|---|---|---|
| C14-15 linear alcohol 7EO | 2.0 | 10.0 |
| Citric acid | 10.0 | 5.0 |
| PARP2 | 2.0 | — |
| PARP4(c) | — | 4.0 |
| DTPMP | — | 1.0 |
| Dye | 2.0 | 1.0 |
| Perfume | 3.0 | 3.0 |
| NaOH | | pH 6–11 |
| Water and minors | | Up to 100% |

EXAMPLE 26

The following fabric softening compositions are in accordance with the present invention

| Component | A | B | C | D | E | F |
|---|---|---|---|---|---|---|
| DTDMAC | — | — | — | — | 4.5 | 15.0 |
| DEQA | 2.6 | 2.9 | 18.0 | 19.0 | — | — |
| Fatty acid | 0.3 | — | 1.0 | — | — | — |
| HCl | 0.02 | 0.02 | 0.02 | 0.02 | 0.02 | 0.02 |
| PEG | — | — | 0.6 | 0.6 | — | 0.6 |
| Perfume | 1.0 | 1.0 | 1.0 | 1.0 | 1.0 | 1.0 |
| Silicone antifoam | 0.01 | 0.01 | 0.01 | 0.01 | 0.01 | 0.01 |
| PARP 3 | 0.4(c) | 0.1(c) | 0.8(c) | 0.2(c) | 1.0(s) | 0.6(c) |
| Electrolyte (ppm) | — | — | 600 | 1200 | — | 1200 |
| Dye (ppm) | 10 | 10 | 50 | 50 | 10 | 50 |
| Water and minors to balance to 100% | | | | | | |

EXAMPLE 27

The following dryer added fabric conditioner compositions were prepared according to the present invention:

|  | A | B | C | D |
|---|---|---|---|---|
| DEQA(2) | — | — | — | 50.0 |
| DTMAMS | — | — | 26.0 | — |
| SDASA | 70.0 | 70.0 | 42.0 | 35.0 |
| Neodol 45-13 | 13.0 | 13.0 | — | — |
| Ethanol | 1.0 | 1.0 | — | — |
| PARP 4(c) | 1.5 | — | 1.5 | 3.0 |
| PARP 1(c) | — | 0.2 | — | — |
| Perfume | 0.75 | 0.75 | 1.0 | 1.5 |
| Glycoperse S-20 | — | — | — | 10.0 |
| Glycerol monostearate | — | — | 26.0 | — |
| Digeranyl Succinate | 0.38 | 0.38 | — | — |
| Clay | — | — | 3.0 | — |
| Dye | 0.01 | 0.01 | — | — |
| Minors to balance to 100% | | | | |

EXAMPLE 28

The following are non-limiting examples of pre-soak fabric conditioning and/or fabric enhancement compositions according to the present invention which can be suitably used in the laundry rinse cycle.

| Ingredients | A | B | C | D | E | F |
|---|---|---|---|---|---|---|
| Polymer | 3.5 | 3.5 | 3.5 | 3.5 | 3.5 | 3.5 |
| Dye fixative | 2.3 | 2.3 | 2.4 | 2.4 | 2.5 | 2.5 |
| Polyamine | 15.0 | 15.0 | 17.5 | 17.5 | 20.0 | 20.0 |
| Bayhibit AM | 1.0 | 1.0 | 1.0 | 1.0 | 1.0 | 1.0 |
| $C_{12}$–$C_{14}$ dimethyl hydroxyethyl quaternary ammonium chloride | — | 5.0 | 5.0 | — | — | — |
| Fabric softener active | — | — | 2.5 | 2.5 | — | — |
| Genamin C100 | 0.33 | — | 0.33 | 0.33 | 0.33 | — |
| Genapol V4463 | 0.2 | — | 0.2 | 0.2 | 0.2 | — |
| PARP2 | 2.0 | 4.0 | 0.2 | 1.0 | 0.1 | 0.16 |
| Water & minors | balance | balance | balance | balance | balance | balance |

EXAMPLE 29

The following are non-limiting examples of odor-absorbing compositions suitable for spray-on applications:

| | Examples | | | | |
|---|---|---|---|---|---|
| Ingredients | A Wt. % | B Wt. % | C Wt. % | D Wt. % | E Wt. % |
| HPBCD | 1.0 | — | 1.0 | — | 1.2 |
| RAMEB | — | 1.0 | — | 0.8 | — |
| Tetronic 901 | — | — | 0.1 | — | — |
| Silwet L-7604 | — | — | — | 0.1 | — |
| Silwet L-7600 | 0.1 | — | — | — | 0.1 |
| Bardac 2050 | — | — | — | 0.03 | — |
| Bardac 2250 | — | 0.2 | — | — | 0.1 |
| Diethylene glycol | — | 1.0 | — | — | 0.2 |
| Triethylene glycol | — | — | 0.1 | — | — |
| Ethanol | — | — | — | — | 2.5 |
| Perfume 1 | 0.1 | — | — | — | — |
| Perfume 2 | — | 0.05 | — | 0.1 | — |
| Perfume 3 | — | — | 0.1 | — | 0.1 |
| Kathon | 3 ppm | 3 ppm | 3 ppm | 3 ppm | — |
| HCl | to pH 4.5 | to pH 4.5 | to pH 3.5 | to pH 3.5 | to pH 3.5 |
| PARP2 | 5.0 | 2.0 | 1.0 | 0.2 | 0.16 |
| Distilled water | Bal. | Bal. | Bal. | Bal. | Bal. |

The perfume 1, 2, and 3 have the following compositions:

| | Perfume | | |
|---|---|---|---|
| Perfume Ingredients | 1 Wt. % | 2 Wt. % | 3 Wt. % |
| Anisic aldehyde | — | — | 2 |
| Benzophenone | 3 | 5 | — |
| Benzyl acetate | 10 | 15 | 5 |
| Benzyl salicylate | 5 | 20 | 5 |
| Cedrol | 2 | — | — |
| Citronellol | 10 | — | 5 |
| Coumarin | — | — | 5 |
| Cymal | — | — | 3 |
| Dihydromyrcenol | 10 | — | 5 |
| Flor acetate | 5 | — | 5 |
| Galaxolide | 10 | — | — |
| Lilial | 10 | 15 | 20 |
| Linalyl acetate | 4 | — | 5 |
| Linalool | 6 | 15 | 5 |
| Methyl dihydro jasmonate | 3 | 10 | 5 |
| Phenyl ethyl acetate | 2 | 5 | 1 |
| Phenyl ethyl alcohol | 15 | 15 | 20 |
| alpha-Terpineol | 5 | — | 8 |
| Vanillin | — | — | 1 |
| Total | 100 | 100 | 100 |

What is claimed is:

1. A process for producing an amine reaction product comprising the steps of:
    a.) contacting, at a temperature of from 5° C. to 80° C., a polyethyleneimine with an active ketone and/or aldehyde material, in the absence of solvent and/or drying agent, to form a reaction mixture comprising an amine reaction product;
    b.) recovering said amine reaction product from said mixture; and
    c.) processing said amine reaction product with a carrier to form a particle.

2. A process according to claim 1, wherein said contacting step is conducted at a temperature range of from 15° C. to 60° C.

3. A process according to claim 1, wherein said reaction mixture is maintained at a substantially constant temperature.

4. A process according to claim 1, wherein said contacting occurs in a twin screw extruder or mixing tank.

5. A process according to claim 1, wherein said active ketone and/or aldehyde material is selected from the group consisting of a flavour ketone or aldehyde ingredient, a pharmaceutical ketone or aldehyde active, a biocontrol ketone or aldehyde agent, a perfume ketone or aldehyde component, a refreshing cooling ketone or aldehyde agent and mixtures thereof.

6. A process according to claim 1, wherein said active ketone and/or aldehyde material is selected from the group consisting of an insect repellant, moth repellant or mixtures thereof.

7. A process according to claim 1, wherein said active ketone and/or aldehyde material comprises an antimicrobial.

8. A process according to claim 1, wherein said active ketone and/or aldehyde material comprises a perfume selected from the group consisting of alpha-damascone, delta damascone, Carvone, Gamma-Methyl-Ionone; Damascenone, hedione, 2,4-dimethyl-3-cyclohexen-1-carboxaldehyde, Florhydral, Lilial, heliotropine, trans-2-nonenal, citral, and mixtures thereof.

9. A process according to claim 1, wherein said carrier has a melting point between 35° C. and 135° C.

10. A process according to claim 9, wherein said particle is treated to form a coated particle.

11. A process according to claim 1, wherein said carrier has a melting point of less than 30° C.

12. A process according to claim 11, wherein said particle is treated to form a coated particle.

13. A process according to claim 1, wherein said carrier is an acid carrier.

14. A process according to claim 13, wherein said particle is treated to form a coated particle.

15. A composition comprising the amine reaction product of claim 9.

16. A composition according to claim 15, said composition being a laundry composition, hard surface cleaning composition or personal cleaning composition.

17. A process for producing an amine reaction product comprising the steps of:
- a.) contacting, in a twin screw extruder or mixing tank, at a temperature of from 5° C. to 80° C., a polyethyleneimine with an active ketone and/or aldehyde material, in the absence of solvent and/or drying agent, to form a reaction mixture comprising an amine reaction product; and
- b.) optionally, recovering said amine reaction product from said mixture.

18. An amine reaction product produced by the process of:
- a.) contacting, at a temperature of from 5° C. to 80° C., a polyethyleneimine with an active ketone and/or aldehyde material, in the absence of solvent and/or drying agent, to form a reaction mixture comprising an amine reaction product;
- b.) optionally, recovering said amine reaction product from said mixture; and
- c.) processing said reaction mixture or said amine reaction product with a carrier having a melting point between 30° C. and 135° C. to form a particle.

19. An amine reaction product produced by the process of claim 18 said process comprising treating said particle to form a coated particle.

20. An amine reaction product produced by the process of:
- a.) contacting, at a temperature of from 5° C. to 80° C., a polyethyleneimine with an active ketone and/or aldehyde material, in the absence of solvent and/or drying agent, to form a reaction mixture comprising an amine reaction product;
- b.) optionally, recovering said amine reaction product from said mixture; and
- c.) processing said reaction mixture or said amine reaction product with a carrier having a melting point of less than 30° C. to form a particle.

21. An amine reaction product produced by the process of claim 20 said process comprising treating said particle to form a coated particle.

22. An amine reaction product produced by the process of:
- a.) contacting, at a temperature of from 5° C. to 80° C., a polyethyleneimine with an active ketone and/or aldehyde material, in the absence of solvent and/or drying agent, to form a reaction mixture comprising an amine reaction product;
- b.) optionally, recovering said amine reaction product from said mixture; and
- c.) processing said reaction mixture or said amine reaction product with an acid carrier.

23. An amine reaction product produced by the process of claim 22 said process comprising treating said particle to form a coated particle.

* * * * *